US 8,306,830 B1
Nov. 6, 2012

(12) United States Patent
Renuart et al.

(10) Patent No.: US 8,306,830 B1
(45) Date of Patent: Nov. 6, 2012

(54) DIRECTED MEDICAL CARE SYSTEM AND METHOD

(76) Inventors: Donald J. Renuart, Avon, OH (US); John M. Cachat, Avon, OH (US)

( * ) Notice: Subject to any disclaimer, the term of this patent is extended or adjusted under 35 U.S.C. 154(b) by 1285 days.

(21) Appl. No.: 11/801,568

(22) Filed: May 10, 2007

Related U.S. Application Data

(60) Provisional application No. 60/799,869, filed on May 12, 2006.

(51) Int. Cl.
*G06Q 10/00* (2012.01)
(52) U.S. Cl. .......................................................... 705/2
(58) Field of Classification Search ........................ None
See application file for complete search history.

(56) References Cited

U.S. PATENT DOCUMENTS

| | | |
|---|---|---|
| 5,241,466 A | 8/1993 | Perry et al. |
| 5,441,309 A | 8/1995 | D'Alessio et al. |
| 5,664,109 A | 9/1997 | Johnson et al. |
| 5,823,948 A * | 10/1998 | Ross et al. ................... 600/300 |
| 6,246,991 B1 | 6/2001 | Abe et al. |
| 2001/0051883 A1 | 12/2001 | Loveland |
| 2003/0036683 A1* | 2/2003 | Kehr et al. ................... 600/300 |
| 2003/0040939 A1 | 2/2003 | Tritch et al. |
| 2005/0086073 A1 | 4/2005 | Rodes et al. |
| 2005/0278195 A1* | 12/2005 | Getz .............................. 705/2 |

\* cited by examiner

*Primary Examiner* — Valerie Lubin
(74) *Attorney, Agent, or Firm* — D. Peter Hochberg; Sean F. Melllino; Daniel J. Smola

(57) ABSTRACT

A system and method of preparing medical care instructions for an individual in an emergency situation. The system and method includes obtaining patient information, providing a mechanism to educate the individual on medical and legal terms and procedures, to create medical care instructions, applying the patient information to applicable legal and medical standards and providing a mechanism for updating and maintaining the medical care instructions. The system and method further includes storing the medical care instructions in electronic format, such as on a central computerized database, and allowing immediate and secure access to the stored medical care instructions by medical personnel. The stored medical care instructions may also be outputted when necessary.

17 Claims, 29 Drawing Sheets

| FULL CODE | ( )YES | ( )NO |
|---|---|---|
| DNR-CC   (Comfort Care) | ( )YES | ( )NO |
| DMC   (Directed Medical Care) | ( )YES | ( )NO |

FIG-7

SHORT TERM CRITICAL CARE: < 1 WEEK

|  | Yes | No |
|---|---|---|
| Mechanical Ventilation |  |  |
| CPR/Defibrillation |  |  |
| Cardioversion |  |  |
| Feeding Tube – Nasogastric |  |  |
| Feeding Tube – Surgical |  |  |
| Dialysis |  |  |
| Surgeries |  |  |
|     Surgery–Neurosurgery |  |  |
|     Surgery–Cardiac |  |  |
|     Surgery–Abdominal |  |  |
|     Surgery–Orthopedic |  |  |
|     Surgery–Tracheostomy |  |  |
| Defer all Surgical Decisions to Family/POC |  |  |
| Invasive Procedures |  |  |
|     Pacemaker |  |  |
|     Stenting–cardiac |  |  |
|     Stenting–vascular/other |  |  |
|     biopsy |  |  |
|     ICP monitor |  |  |
|     Suprapubic catheter |  |  |
| Defer all Invasive Procedure Decisions to Family POC |  |  |

DNR-CC

| We Will Do |
|---|
| Pain Management |
| Oxygen and Airway Suction |
| Splint Fractures |
| Repair Lacerations |
| Check and Correct Low Blood Sugar |
| Position of Comfort |

| Optional | Yes | No |
|---|---|---|
| Take to Hospital | | |
| Fever – Look for and Treat Infection | | |
| Nausea/Vomiting Treat Symptoms | | |
| Nausea/Vomiting Look for Cause | | |
| GI Bleeding – Look for and Treat Cause | | |
| Transfuse Blood Product | | |
| Stroke – Work Up | | |
| Chest Pain – Work Up | | |
| Abdominal Pain – Work Up | | |
| Electrolytes – Look for and Treat Abnormalities | | |
| Low BP – Treat with Fluids | | |
| Low BP – Treat with IV Medications | | |
| High BP – Treat with Medications | | |
| Tachycardia – Treat with Medications | | |
| Tachycardia – Treat with Cardioversion | | |
| Bradycardia – Treat with Medications | | |
| Bradycardia – Treat with Pacing | | |
| DVT – Work Up and Treatment | | |
| Seizure – Work Up | | |
| Mental Status Change – Work Up | | |

FROM
FIG-11A

| Surgery | Yes | No |
|---|---|---|
| Leave to Family/POC Discretion | | |
| Acute Abdomen | | |
| Hip or Bone Fracture | | |
| Decompress Intracranial Hemorrhage | | |
| Pacemaker Placement | | |
| Cardiac Cath | | |
| Pulseless Extremity | | |
| Surgical Feeding Tube Placement | | |
| Surgical Airway – Tracheostomy | | |

| Cost Savers | Yes | No |
|---|---|---|
| Transfer to Hospital | | |
| CT Head | | |
| CT Abdomen | | |
| CT Chest | | |
| Endoscopy/Colonoscopy | | |
| Cardiac Echo | | |
| Carotid Duplex | | |
| MRI | | |
| Scrutinize Medication List | | |
| Cardiac Catherization | | |
| Ultrasound Extremity for DVT | | |

| Organ Donation | Yes | No |
|---|---|---|
| Post Death Educational Procedures | | |
| Organ Donation for Recipient Use Only | | |
| Medical Education – No Resale | | |
| All Medical Uses | | |

FIG-11B

DNR-CC

| We Will Do |
|---|
| Pain Management |
| Oxygen and Airway Suction |
| Splint Fractures |
| Repair Lacerations |
| Check and Correct Low Blood Sugar |
| Position of Comfort |

| Optional | Yes | No |
|---|---|---|
| Take to Hospital | X | |
| Fever – Look for and Treat Infection | X | |
| Nausea/Vomiting Treat Symptoms | | X |
| Nausea/Vomiting Look for Cause | | X |
| GI Bleeding – Look for and Treat Cause | | X |
| Transfuse Blood Product | | X |
| Stroke – Work Up | X | |
| Chest Pain – Work Up | X | |
| Abdominal Pain – Work Up | | X |
| Electrolytes – Look for and Treat Abnormalities | X | |
| Low BP – Treat with Fluids | | X |
| Low BP – Treat with IV Medications | | X |
| High BP – Treat with Medications | | X |
| Tachycardia – Treat with Medications | X | |
| Tachycardia – Treat with Cardioversion | | X |
| Bradycardia – Treat with Medications | | X |
| Bradycardia – Treat with Pacing | | X |
| DVT – Work Up and Treatment | | X |
| Seizure – Work Up | | X |
| Mental Status Change – Work Up | | X |

FROM
FIG-12A

| Surgery | Yes | No |
|---|---|---|
| Leave to Family/POC Discretion | | X |
| Acute Abdomen | | X |
| Hip or Bone Fracture | X | |
| Decompress Intracranial Hemorrhage | | X |
| Pacemaker Placement | | X |
| Cardiac Cath | | X |
| Pulseless Extremity | | X |
| Surgical Feeding Tube Placement | X | |
| Surgical Airway – Tracheostomy | X | |

| Cost Savers | Yes | No |
|---|---|---|
| Transfer to Hospital | | X |
| CT Head | | X |
| CT Abdomen | | X |
| CT Chest | | X |
| Endoscopy/Colonoscopy | | X |
| Cardiac Echo | X | |
| Carotid Duplex | | X |
| MRI | X | |
| Scrutinize Medication List | | X |
| Cardiac Catherization | | X |
| Ultrasound Extremity for DVT | | X |

| Organ Donation | Yes | No |
|---|---|---|
| Post Death Educational Procedures | | X |
| Organ Donation for Recipient Use Only | | X |
| Medical Education – No Resale | | X |
| All Medical Uses | X | |

FIG-12B

SHORT TERM CRITICAL CARE: < 1 WEEK

| | Yes | No |
|---|---|---|
| Mechanical Ventilation | X | |
| CPR/Defibrillation | | X |
| Cardioversion | X | |
| Feeding Tube – Nasogastric | X | |
| Feeding Tube – Surgical | | X |
| Dialysis | | X |
| Surgeries | X | |
|     Surgery-Neurosurgery | X | |
|     Surgery-Cardiac | | X |
|     Surgery-Abdominal | | X |
|     Surgery-Orthopedic | | X |
|     Surgery-Tracheostomy | | X |
| Defer all Surgical Decisions to Family/POC | X | |
| Invasive Procedures | X | |
|     Pacemaker | | X |
|     Stenting-cardiac | | X |
|     Stenting-vascular/other | X | |
|     biopsy | | X |
|     ICP monitor | | X |
|     Suprapubic catheter | | X |
| Defer all Invasive Procedure Decisions to Family POC | | X |

FROM
FIG-14B

INTERMEDIATE TERM CRITICAL CARE: < 1-3 WEEKS

|  | Yes | No |
|---|---|---|
| Mechanical Ventilation | X |  |
| CPR/Defibrillation |  | X |
| Cardioversion | X |  |
| Feeding Tube – Nasogastric | X |  |
| Feeding Tube – Surgical |  | X |
| Dialysis |  | X |
| Surgeries | X |  |
| Surgery–Neurosurgery | X |  |
| Surgery–Cardiac |  | X |
| Surgery–Abdominal |  | X |
| Surgery–Orthopedic |  | X |
| Surgery–Tracheostomy |  | X |
| Defer all Surgical Decisions to Family/POC | X |  |
| Invasive Procedures | X |  |
| Pacemaker |  | X |
| Stenting–cardiac |  | X |
| Stenting–vascular/other | X |  |
| biopsy |  | X |
| ICP monitor |  | X |
| Suprapubic catheter |  | X |
| Defer all Invasive Procedure Decisions to Family POC |  | X |

DIRECTED MEDICAL CARE SYSTEM AND METHOD

CROSS-REFERENCE TO RELATED APPLICATION

This application claims priority of U.S. Provisional Application No. 60/799,869, filed May 12, 2006, under Title 35, United States Code, Section 119(e).

BACKGROUND OF THE INVENTION

1. Field of the Invention

The present invention relates generally to medical care management systems. More particularly, the present invention relates to a directed medical care expert system and method for educating and guiding an individual through a process of making difficult and complicated end-of-life decisions and creating a comprehensive and accessible medium, such as a document, for easily directing medical personnel to provide a particular level of medical care chosen by the individual and which provides medical personnel with answers to vital medical-related questions for providing care and/or treatment during an individual's medical emergency. The subject invention relates also to a medical care management system and method that controls access, storage, revision, maintenance and immediate distribution of medical care instructions created by the expert medical care system.

2. Description of the Prior Art

The current system of living wills, do not resuscitate orders (DNR's) and advance directives is fragmented, non-uniform out-dated and fails to provide appropriate medical information to medical personnel for assisting in providing medical treatment to an individual. The current system also lacks a mechanism for educating an individual for making the most appropriate decisions for the particular individual's medical situation or which are best in line with the individual's specific desires. Furthermore, the current system lacks the ability to change, amend or otherwise update the individual's decisions for medical care treatment and for providing medical personnel immediate access to those changes. Still further, the present system lacks transportability of medical care decisions so that the medical care directives are either able to be easily transported on an individual's person or is easily and immediately obtained by medical personnel. An issue which must be addressed is that many individuals arrive at a hospital without advance medical directives.

Patients checking into hospitals and clients meeting with their lawyers often are advised to take a simple step toward planning for the future by preparing a living will. The intent is good; however, the reality of living wills is they do not sufficiently work. A living will might direct that no extraordinary measures be used if a person's condition is terminal. Since the terms "extraordinary measure" and "terminal" are often not defined, confusion may arise. In turn, medical personnel often times avoid referring to the medical directives set forth in a living will in order to avoid confusion. Yet another issue which arises is that many living wills are vague and lack the appropriate medical information, thereby essentially rendering them useless in many instances.

Standard DNR orders attempted to simplify the process by presenting an individual with only three different choices. In theory, this system is beneficial since it is relatively simple. However, such simplicity has shown to be disadvantageous since there are too many presenting scenarios and categorizing these scenarios into one of three choices is unrealistic. Because of this, DNR documents are also often times ignored by medical personnel.

In addition, standard DNR orders or other medical directive documents, lack transportability and immediate availability to medical personnel. As noted above, this renders such documents useless since they are often times not available at the time of need, which in turn means that the individual's emergency and/or end-of-life desires are not met and the individual's wishes for resuscitation are not available.

The concept seems to be straightforward: an individual should outline his or her wishes while he or she is healthy in order to guide doctors and family members who might have to make life or death decisions for the individual at a later time. A typical question that an advance medical directive should answer is whether a person would want to linger in a vegetative state if it were unlikely he or she would ever recover, or would that person prefer to be allowed to die? Clearly, end-of-life medical questions often involve complicated medical decisions.

Another typical question involves the situation where a person is suffering from an end-stage disease and whether that person would want treatment if the treatment would only provide a minimal chance of extending the person's life or would only extend the person's life for a short period of time, i.e., a few days to a few weeks For example, should an end-stage Alzheimer's patient who has signed a DNR comfort care order (which typically do not include a provision for antibiotics), whose life is greatly diminished but still has moments of joy and conversation, be given the option for use of antibiotics to treat an infection that if left untreated might cause the person's death?

There are other problems as well. For example, people often change their minds after they write their advance medical directives, but neglect to update the advance directives to reflect these changed desires. Furthermore, many advance directives (or living wills) never arrive to the patient's bedside, but rather are left in a file cabinet or safety deposit box or are even lost or misplaced. Moreover, even if the living will is available, family and doctors often have difficulty in deciphering the patient's wishes due to the inherent ambiguity and lack of appropriate medical information set forth in the documents. As noted above, most times these documents do not accompany the patient to the hospital, and therefore are not readily accessible, thereby rendering the documents moot.

An additional issue that arises relates to the fact that most individuals are not familiar with most medical and/or legal terms and procedures which deal with end-of-life decisions. For example, an individual might assume based on preconceived notions that being placed on a respirator should be avoided regardless of the medical emergency situation. In reality, the individual might not understand that in certain situations a respirator might simply facilitate recovery from an illness which might otherwise cause the person's death. However, not having access to this information may result in the patient making an uneducated or poorly informed medical decision, in which case the individual may reject a particular treatment, such as placement on a respirator. In this case, the individual would reject treatment which could potentially facilitate recovery, and consequently, the person suffers a premature death. Having access to the information for making a fully informed and educated decision might cause the individual to reconsider the decision to not be placed on a respirator regardless of the medical emergency situation. Therefore, there is a need for providing an individual with the information and education necessary to fully understand the decisions which are set forth in the medical directives in an easily understood and accessible manner.

Another issue which must be addressed is the overwhelming concern about litigation. Since 1990, most states require hospitals to offer all patients a chance to prepare a living will. Despite the law and despite several high-profile end-of-life legal disputes, most people still do not have some form of advance medical directive. Thus, there is a need for a system and method for guiding and educating an individual through the process of end-of-life decisions and creating a comprehensive medium, such as a document to easily direct a medical care provider to grant a level of care chosen by the individual. There is also a need for a medical care management system and method that control access, storage and revisions, along with immediate distribution of the medical care instructions created by the medical care system. The subject invention overcomes the above-noted limitations and provides a system and method for guiding and educating an individual through the process of making end-of-life medical decisions and creating a comprehensive document to easily direct the medical care provider to grant the level of care chosen by the individual. The subject invention also presents a management system and method that control access, storage, revision, maintenance, immediate distribution and timing of medical care instructions created by the medical care system, and that guide the medical care provider to grant the particular level of care chosen by the individual.

Yet another issue which must be addressed pertains to post-death organ donation. Many individuals may not have considered the option of organ donation once the individual has passed away. Moreover, many individuals may not sufficiently understand the process of organ donation or they may believe that organ donation only means that the organs are donated to other individuals in need of new organs. However, there is a tremendous need for relatively healthy organs to be donated to assist other individuals who are still living. In addition, there is a need for organs to be donated for scientific research purposes. Therefore, there is a need for providing an individual with the information necessary to fully understand organ donation and all possible options for donating organs for post-death use, as well as for assisting the individual in making organ donation decisions and making those decisions readily accessibly to medical personnel. The current system for organ donation is fragmented and lacks an appropriate mechanism for educating individuals or documenting the individual's decisions.

An example of a prior art living will storage is set forth in U.S. Pat. No. 5,241,466 (Perry, et al.). Perry, et al. discloses a central depository for storage and retrieval of important documents and information, such as living wills, and other related documents. The depository includes a data storage facility having a computer and WORM drive CD-ROM player connected to an optical scanner. The relevant documents are scanned by the optical scanner and stored on the CD-ROM player. Requests for information can be received by the depository from remote locations by data transmission devices. The system also provides a procedure for updating the information and documents as legislation regarding the stored information and documents changes, as well monitors for changes in residence which may affect the information and documents. A disadvantage with the Perry, et al. prior art system is that it fails to provide a procedure or mechanism for educating or otherwise providing information to an individual to facilitate the process of making fully informed end of life decisions.

SUMMARY OF THE INVENTION

The subject invention is particularly suited to a directed medical care expert system and method to be used in a medical care management system. It should be appreciated that this system can be made immediately available/accessible to the medical care team in real time upon request to provide the level of care chosen by the individual and will help eliminate unwanted and costly attempts at resuscitation, as well as the undesired prolonging of death by the use of breathing machines and feeding tubes or other measures. The real time information will be delivered to the medical care team in settings such as, but not limited to, pre-hospital care (i.e., EMS), emergency room, hospital care and nursing home care. The medical care information may be immediately accessible by medical personnel from any location at any time via accessing a central database or an Internet website. The medical care information may also be obtainable by medical personnel by downloading the relevant documents from the main storage database. However, it should be appreciated that the subject system has broader applications to any medical assistance management, including management of services at schools, public venues, personal residences, nursing homes, hospices, and the like. It should also be appreciated that the disclosed system is advantageously used in connection with aged, terminal patients, physically or mentally challenged individuals and youth, as well as any group that stands to benefit by pre-planned procedures or methodology, particularly in connection with assisted services.

In accordance with the present invention, there is provided a directed medical care system and method. Further, in accordance with the present invention, there is provided a medical care expert system and method for guiding an individual through the process of end-of-life decisions, defining medical and/or legal terms and procedures, explaining medical and/or legal terms and procedures, creating a comprehensive document or other medium to easily direct a medical care provider to offer a level of care chosen by the individual and maintaining/updating the medical care directives according to applicable legal changes and/or changes in the individual's medical care decisions. Still further, in accordance with the present invention, there is provided a medical care management system and method for guiding the medical care provider to offer the level of care chosen by the individual that controls access and distribution of medical care instructions created by the medical care expert system.

The subject invention provides a specific approach to helping people define their wishes. Provided is an interactive process that takes a patient through a variety of scenarios to help him or her understand and more clearly state his or her desires. The process may be available, for example, on a CD-ROM for home use and/or via an Internet website. The medical care instructions created through the interactive process may be stored on a central website database to provide immediate access to allow the medical personnel to ensure that the patient's wishes are followed and to allow the individual with a relatively simply mechanism for updating the medical care decisions.

The present invention addresses the issues of lack of transportability and individuals making uneducated medical care decisions and uneducated post-death organ donation decisions. The present invention incorporates, educates, creates, controls access to, stores, revises and distributes the individual's wishes as recorded in the medical care directives document. The present invention is a dynamic web-based (or other electronic format-based, e.g., compact disc,) live interactive process to educate, guide and create a unique medical care directive document. The document provides medical personnel with answers to specific medical care questions in a quick and user-friendly format. The document of the present invention combines decisional pathways for acute care, intermediate care and long-term care. The document also integrates a newly devised organ donation pathway. The present invention further provides real time interaction for revisions and updates and provides active reminders to the individuals to review and/or update the medical directives on a predetermined (or pre-set default) schedule.

It is an object of the present invention to provide an improved system for replacing ineffective living wills.

Another object of the present invention is to provide an improved directed medical care system having an improved mechanism for educating individuals regarding medical and/or legal terms and procedures.

Yet another object of the present invention is to eliminate, or at least reduce, the amount of interpretation of directed medical care instructions by medical personnel and/or an individual's family members, thereby improving the overall autonomy of an individual once a situation occurs which requires directed medical care.

Still yet another object of the present invention is to providing an individual with a mechanism for easily updating his or her medical care directives, as well as a mechanism for alerting the individual on a periodic basis that updates and/or maintenance might be necessary.

Still other objects and aspects of the present invention will become readily apparent to those skilled in the art from the following description wherein there is shown and described a preferred embodiment of the present invention, simply by way of illustration of one of the best modes suited to carry out the invention. As it will be realized, the invention is capable of other different embodiments, and its several details are capable of modifications in various obvious aspects all without deviation from the invention. Accordingly, the drawings and descriptions should be regarded as illustrative in nature and not as restrictive.

BRIEF DESCRIPTION OF THE DRAWINGS

The accompanying drawings incorporated in and forming a part of the specification illustrate several aspects of the present invention and together with the description, serve to explain the principles of the invention. In the drawings:

FIG. 7 is an exemplary selection chart providing possible emergency care options for a patient.

FIG. 11 is an exemplary selection chart for providing end-of-life selections for a patient in a comfort care situation.

FIG. 12 is an exemplary output chart for a patient in a comfort care situation.

DETAILED DESCRIPTION OF THE PREFERRED EMBODIMENT

Preferred embodiments of the present invention disclose an improved directed medical care expert system and method for guiding and educating an individual to create medical care instructions, maintenance of the medical care instructions and a directed medical care management system and method that control access and distribution of medical care instructions created by the medical care expert system. However it should be appreciated that the methods and apparatus disclosed herein are advantageously applied to any health management system in which decisions are required to be made relative to any subject care situation that is hierarchically dependent on a series of questions and inquiries that allow for informed and educated decisions to be made for care and transition issues relative to any individual. More particularly, this invention discloses a directed medical care system and a method for guiding an individual through the process of making difficult end-of-life decisions and creating a comprehensive document to easily direct medical personnel to provide a level of care chosen by the individual, as well as readily providing the documents to medical personnel. Also disclosed is a system for allowing an individual to easily maintain the created medical care decisions as desired. Further details of the system and of the method are set forth in the enclosed drawings and charts.

Figure 1:
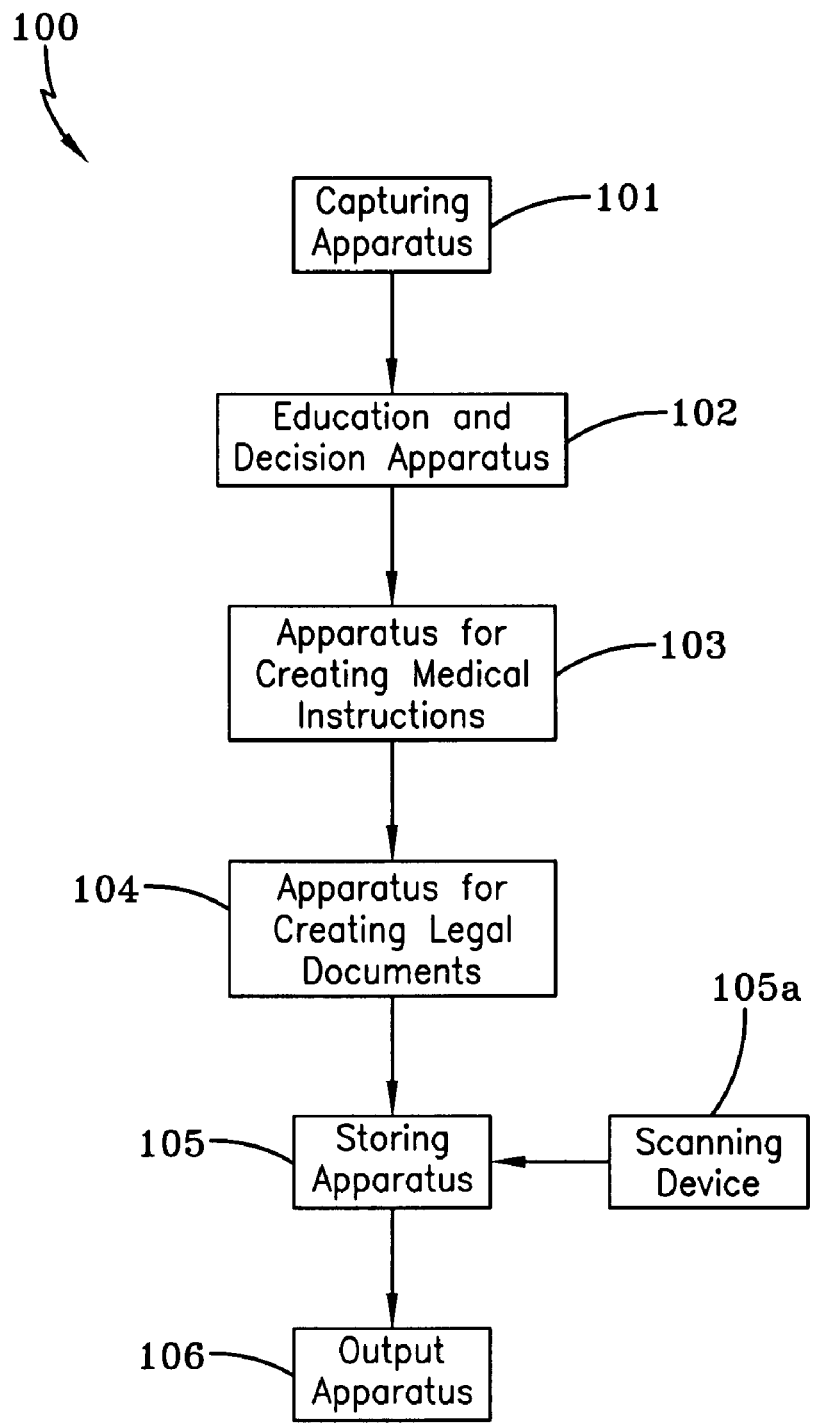
FIG. 1 is a block diagram of the directed medical care expert system for guiding an individual to create medical care instructions.
Figure 2:
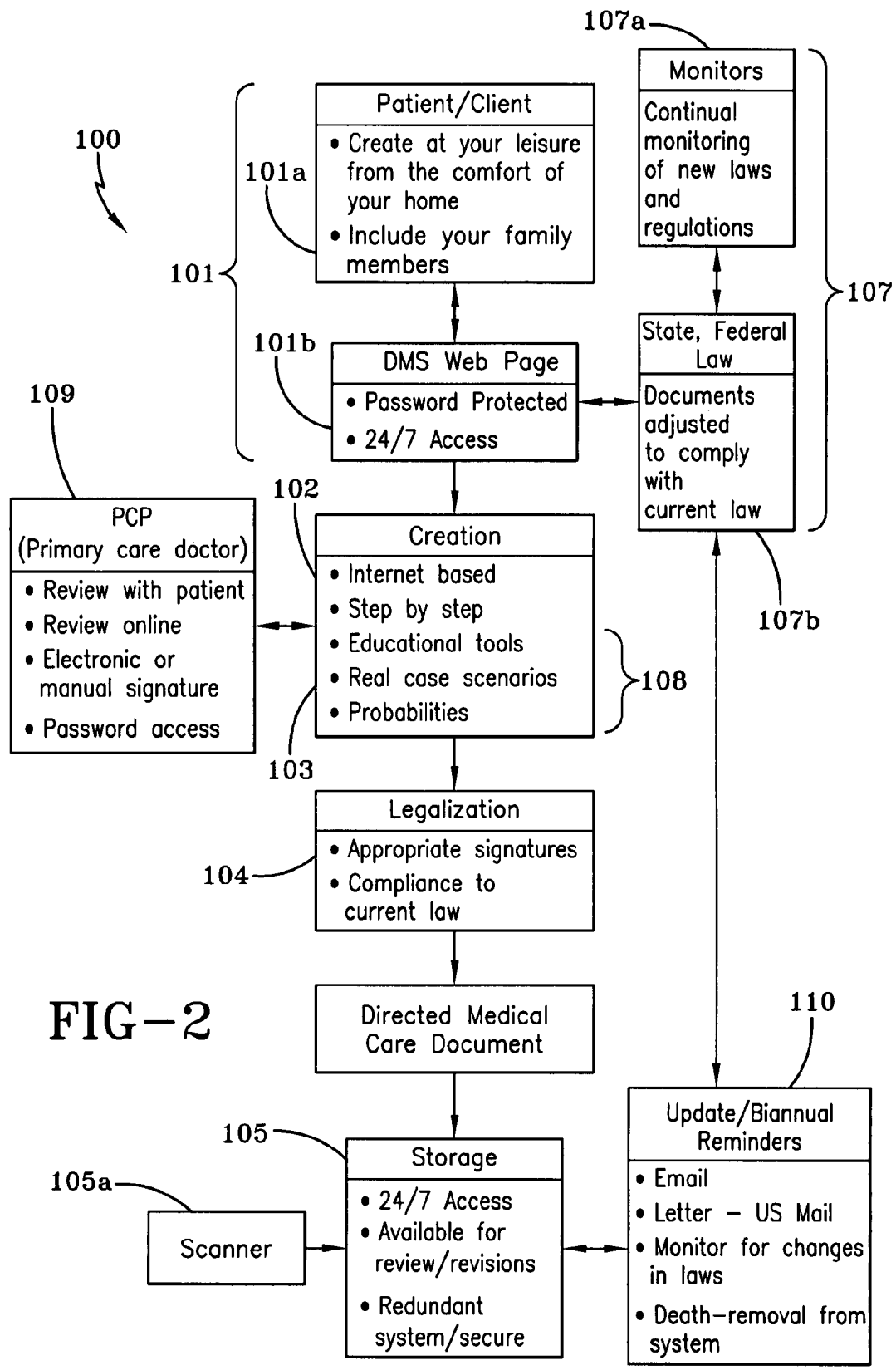
FIG. 2 is a flow chart of the directed medical care system for guiding an individual to create medical care instructions.

Referring to FIG. 1 and FIG. 2, there is shown an exemplary embodiment of the directed medical care expert system 100 for guiding an individual to create medical care instructions. The directed medical care expert system 100 includes a personal information capturing apparatus 101 for capturing (or inputting) personal information of an individual, an education and decision-recording apparatus 102 for educating an individual on legal and medical terms and procedures and recording decisions on a chosen level of medical care with respect to a relevant emergency issue, a medical care instructions creation apparatus 103 for creating medical care instructions, a legal documents creation apparatus 104 for creating legal documents, a storing apparatus 105 for storing created medical care instructions and created legal documents, and an output apparatus 106 for outputting created medical care instructions and created legal documents. As discussed further below, an updating and maintenance apparatus is also provided for updating the created medical care documents. Personal information capturing apparatus 101, education and decision-recording apparatus 102, medical care instructions creation apparatus 103, legal documents creation apparatus 104, storing apparatus 105, and outputting apparatus 106 are suitably interconnected through a network using any communications links known in the art, or even may be devices cooperatively integrated with one another, at least in part. In the case of the latter, an interface apparatus, discussed below with relation to FIG. 3, may be provided for interfacing and integrating each of the aforementioned components together. As will be understood by those skilled in the art, the communications link is any device for communication between electronic devices, including for example and without limitation, an Ethernet based network, an infrared connection, a Wi-Fi connection, a telephone connection, a cellular connection, a Bluetooth connection and the like, or any combination of the aforementioned communication devices.

Personal information capturing apparatus 101 captures personal information (or background information) of an individual. Capturing personal information of an individual may be done in person, by witnesses, care givers, etc., or may be done by the individual himself or herself. This should be done in advance by the individual or during an interview with a doctor, or with a medical care expert for assistance. In some cases the personal information might have to be updated during the medical care procedure. Capturing personal information is set forth at step 101*a* (FIG. 2) and subsequently may include without limitation answering personal information questions, with the answers being electronically stored, e.g., on a CD-ROM or on a website database, or electronically stored from an interview with the doctor or another medical care expert at step 101*b* (FIG. 2). It should be appreciated that the central website database for storing personal information would be accessible by the individual (or other authorized person) at all times and would be protected via a secure connection and a password. Questions are related in subject matter, for example, and without limitation, to individual identification data, to a medical condition(s) of the individual, medical history of the individual, insurance data associated with the individual, etc. The interview may include demonstrative educational videos with website links with examples and expert explanation, or the individual can use demonstrative educational videos independently for educating the individual on medical and/or legal terms and medical procedures. The individual may also use a personal computer with a friendly graphical user interface, which explains alternatives and the potential impact of a respective decision.

Education and decision-recording apparatus 102 educates individuals on potential decisions and records decisions made by the individual (or an authorized person) on a chosen level of medical care with respect to a relevant emergency issue, and is representative of expert rules for facilitating the individual to make decisions on a chosen level of medical care. The expert rules may be retained, e.g., on a CD-ROM or website. The individual may use a personal computer with a user-friendly graphical user interface or may make his or her decisions using a hardcopy document containing expert rules. It should be appreciated that a monitoring apparatus 107 is provided for monitoring the expert rules 107*a* (FIG. 2) and updating 107*b* (FIG. 2) by including international legal changes, federal legal changes, state legal changes, new medical best practices and updated care alternatives and explanations. Accordingly, the resulting decisions/documents of the individual are updated and adjusted 107*b* in order to maintain, amend or update the documents in compliance with any changes to the applicable Federal and/or state laws.

Still referring to FIG. 1 and FIG. 2, education and decision recording apparatus 102 is provided with devices for educating an individual regarding any medical and/or legal terms or procedures which are addressed by medical care expert system 100. For example, an information providing apparatus 108 is provided with education and decision recording apparatus 102 for explaining medical and/or legal terms and procedures to the individual. Information providing apparatus 108 may be provided integral with education and decision recording apparatus 102 or may be provided as a supplement to education and decision recording apparatus 102. In other words, in the case where education and decision recording apparatus 102 is provided as a CD-ROM based system, information providing apparatus 108 may be a supplemental CD-ROM (or other information-containing device) which provides explanation on terms and procedures, such as definitions of terms and procedures, examples of procedures, "real-life" scenarios, potential results/consequences for any particular procedures, step-by-step explanation of the details of any particular medical procedures, etc. Information providing apparatus 108 provides information to an individual in easy-to-understand simple terms (i.e., non-medical terms). For example, an orthopedic surgery is referred to medically as an Instrumental Lumbar Fusion, which could be described in non-medical terms as the fusion of a vertebrae to another part of the back bone with the use of a metal reinforcing rod. In turn, education and decision recording apparatus 102 records decisions in medical/legal terminology. In the case where education and decision recording apparatus 102 is provided as an Internet-based website, information providing apparatus 108 is provided as a website link accessible via, for example, a hyperlink to a related website or database or a downloadable program, which provides explanation on terms and procedures, such as definitions of terms and procedures, examples of procedures, "real-life" scenarios, potential results/consequences for any particular procedures, step-by-step explanation of the details of any particular medical procedures, and the like. Information providing apparatus 108 provides relevant information in the form of drawings, pictures, "real-life" videos/demonstrations, animation videos, expert explanation, and the like. For example, an individual might have to make a decision as to whether he or she would like to be placed on a respirator if an emergency situation occurs. Information providing apparatus 108 provides information to an individual in easy-to-understand simple terms (i.e., non-medical terms) to educate the individual about the process of being placed on a respirator. In turn, education and decision recording apparatus 102 records decisions in medical/legal terminology. The individual may also use a personal computer with a friendly graphical user interface, which explains alternatives and the potential impact of a respective decision. Information providing apparatus 108 also provides information to the individual on post-death options, such as cremation, burial services and/or organ donation.

A review apparatus 109 is provided for reviewing the created medical care instructions for errors and/or omissions. Review apparatus 109 is in electronic communication with education and decision recording apparatus 102 or may be integral with education and decision recording apparatus 102. Review apparatus 109 may be, for example, a mechanism for reviewing the created medical care directives to ensure accuracy and to ensure correct compliance with the applicable Federal and state laws. In addition, review apparatus 109 may be applied by the individual in conjunction with the individual's primary care physician or may be reviewed by the primary care physician (or other authorized medical personnel) at a remote location by accessing the created medical care directives which are in a preliminary form. Alternatively, the preliminary medical care directives could be electronically sent via e-mail to a primary care physician at a remote location for review for accuracy and compliance with applicable laws. It should be appreciated that review of the medical care directives would be password protected and accessible via a secure connection.

After decisions are made and the instructions are reviewed for their accuracy, medical care instructions creation apparatus 103 creates the medical care instructions for the patient. Medical care instructions creation apparatus 103 is in data communication with education and decision-recording apparatus 102, whereupon medical care instructions creation apparatus 103 utilizes the decision results. The medical care instructions may be created in an electronic form for storage in a central accessible database, and/or on paper for printing in the form of a hard-copy. Next, legal documents creation apparatus 104 creates the requisite legal documents, such as powers of attorney, health insurance documents, and other associated documents, if it is necessary to create such documents. Legal documents may include the created medical care instructions, or may have attached to them signatures of the individual and witnesses for legalization. These signatures may be implemented as electronic signatures.

Created medical care instructions and created legal documents are then stored in electronic storing apparatus 105. Storing apparatus 105 is employed as a suitable storage medium accessible via a secure computer network. The storage medium is any storage medium known in the art, including, for example and without limitation, optical storage, magnetic storage, or the like. Storing apparatus 105 may be employed, for example, and without limitation, as a CD-ROM, a USB flash drive, a website or a specific repository. In a case when the medical care instructions and the legal documents are created as hard copy documents on paper, the medical care instructions may be scanned by storing apparatus 105 or by a suitable scanning device (105a) associated with the storing apparatus 105 and subsequently electronically stored for retrieval. Copies of final documents may be outputted by outputting apparatus 106, for example, and without limitation, in the form of a hard copy or e-mail to another repository upon a secure request, to defined relatives, to defined lawyers, to defined financial guardians, to defined insurance personnel, or to specified doctors, nurses, or other qualified medical personnel.

As shown in FIG. 2, an update and reminder apparatus 110 is provided and is in electronic communication with storage apparatus 105, as well as with monitoring apparatus 107. Update and reminder apparatus 110 cooperates with monitoring apparatus 107 for any updated and changes in Federal and state laws and updates the created medical care directives accordingly. Update and reminder apparatus 110 further provides a periodic reminder to the individual, such as once or twice a year as desired by the individual, to remind the individual to review the created medical care directives and to update the directives for any changes which may have occurred. Updates and changes may of course be applied to personal information, medical care directives, the particular level of medical care desired, etc. In addition, update and reminder apparatus 110 monitors whether the individual has had significant changes in his or her medical state which could require review and/or modification of any scheduled procedures and for whether the individual has passed away, in which case the medical care instructions may be removed from the system. For example, update and reminder apparatus 110 may be programmed to recognize that failure by an individual to update the medical care instructions after a particular number of reminders is an indication that the individual has passed away and therefore should be removed from the system. Apparatus 110 alternatively may flag the directives as not having been updated for a particular amount of time. The individual may elect to update the medical directives accordingly, or may decline to update the medical directives. The reminder may be provided to the individual electronically, such as to an e-mail address, to a home address through regular mail notification or by telephone, such as an automated telephone reminder system.

Figure 3:
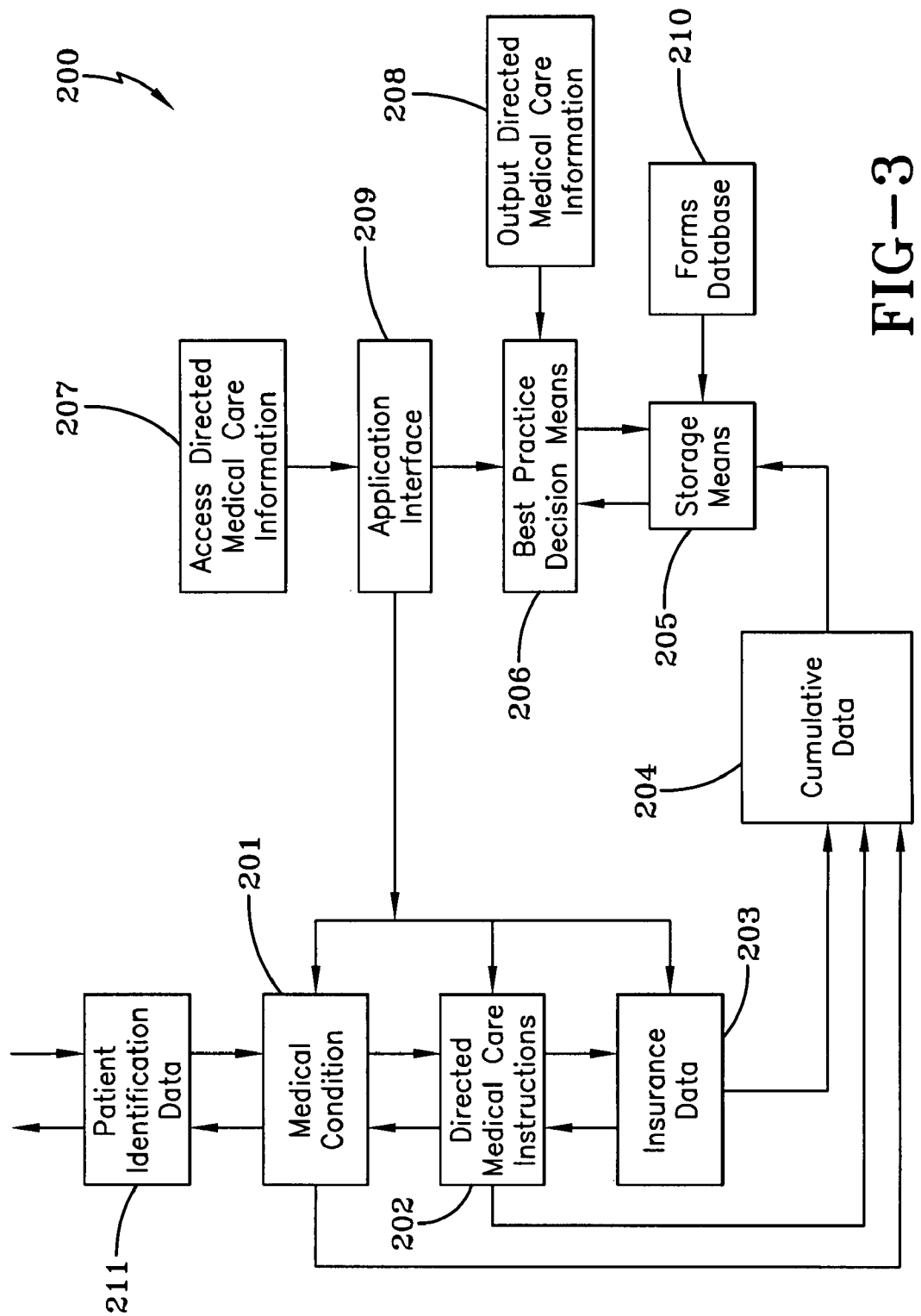
FIG. 3 is a block diagram of the directed medical care management system according to the present invention.

Referring now to FIG. 3, a block diagram of the directed medical care management system according to the present invention is provided and referred to generally at numeral 200. It should be appreciated by those skilled in the art that the directed medical care management system 200 is used by a medical care provider in the event of an emergency issue. In this situation, the medical care provider needs to obtain all necessary information concerning the patient as soon as possible, preferably in a time window of less than 30 minutes. The necessary information includes, without limitation, the patient's identification data (i.e., name, age, birth date, SSN, address, RF tag, finger print, etc), prior medical conditions and medical history, medical prescriptions, designated relatives or care takers, health insurance and accountability data, and a verification of existence of directed medical instructions.

Directed medical care management system 200 includes a medical condition data apparatus 201 to access and receive patient data indicative of a medical condition associated with a patient, an end-of-life decision apparatus 202 to access and receive patient data indicative of an end-of-life decision associated with the patient (i.e., directed medical care instructions), an insurance and accountability data apparatus 203 to access and receive patient data indicative of insurance and accountability data associated with the patient, an integration apparatus 204 to generate cumulative data, a storage apparatus 205 for storing cumulative data, a best practice care decision apparatus 206 for establishing the best practice care for the patient based on directives from the individual, a guardian, a health care provider, etc., an access apparatus 207 for accessing the system 200, and an output apparatus 208 to output the determined best practice care for the patient. System 200 also includes an application interface apparatus 209, as discussed below. It should be appreciated by those skilled in the art that in case of a non-emergency situation, data associated with the patient may be advantageously updated through suggested means for collecting patient data that include, for example and without limitation, personal interviews, phone interviews, the patient's CD or website data with his or her end-of-life decisions, other website data, or the like. For accessing best practice care decision apparatus 206 and/or distributing data through output apparatus 208, any methods known in the art may be used, including, for example and without limitation, radio frequency identification (RFID), barcode tag, fingerprint scanner, retina scan, ID bracelet/necklace, ID card, link to hospital records, link to insurance provider record, link to driver license record, and the like. One or more of the foregoing devices could be used. Storage apparatus 205 for storing data is any storage medium known in the art, including, for example and without limitation, optical storage, magnetic storage, or the like. Data is capable of being stored, for example, as metadata, all of which are referred to as electronic storage. Each of medical condition data apparatus 201, end-of-life decision data apparatus 202, insurance and accountability data apparatus 203, integration apparatus 204, storage apparatus 205, best practice care decision apparatus 206, access apparatus 207, output apparatus 208 and application interface apparatus 209 comprising the directed medical care management system 200 of the present invention may be electronically communicatively coupled over a network environment. System 200 is advantageously integrated with a forms database 210 for storing or retrieving forms or data relative to a patient, as well as a repository for forms that may be necessary or desirable. Such forms suitably include, but are not limited to, insurance forms, governmental forms, legal documents, such as power of attorney documents, payment authorization, and the like, as well as their electronic or on-line equivalents. System 200 also advantageously includes a patient identification data apparatus 211 to access and receive identification data associated with the patient. The identification data may include, without limitation, the patient's name, age, birth date, SSN, address, RF tag, fingerprint, etc.

It should be appreciated by those skilled in the art that a suitable network environment is any distributed communications environment known in the art capable of enabling the exchange of data. The skilled artisan should understand that the network environment is any computer network, known in the art, including for example, and without limitation, a local area network, a wide area network, a personal area network, a virtual network, an intranet, the Internet, or any combination thereof. In the preferred embodiment of the present invention, the computer network is comprised of physical layers and transport layers, as illustrated by the myriad of conventional data transport mechanisms, such as, for example and without limitation, Token-Ring, 802.11(x), Ethernet, or other wire-based or wireless data communication mechanisms.

In operation, a medical care provider accesses system 200 using any methods known in the art, as mentioned above. Through the application interface apparatus 209, the medical care provider accesses medical condition data apparatus 201, end-of-life decision data apparatus 202, insurance and accountability data apparatus 203, and patient identification data apparatus 211 to provide the necessary electronic data to access and receive patient data indicative of a medical condition associated with the patient, patient data indicative of an end-of-life decision that is associated with the patient, and patient data indicative of insurance and accountability data associated with the patient, as well as identification data associated with the patient. Patient data received by medical condition data apparatus 201, end-of-life decision data apparatus 202, insurance and accountability data apparatus 203, and patient identification data apparatus 211 is integrated by integration apparatus 204 for generating cumulative data, which is then stored in storage apparatus 205. Best practice care decision apparatus 206 retrieves cumulative data from storage apparatus 205, the cumulative data being indicative of a medical condition associated with the patient and of an end-of-life decision associated with the patient. Best practice care decision apparatus 206 analyzes the retrieved data and, using a directive via any suitable manner as will be readily understood by one of ordinary skill in the art, determines the best practice care for the patient. The determined best practice care is then outputted by output apparatus 208.

Figure 4A:
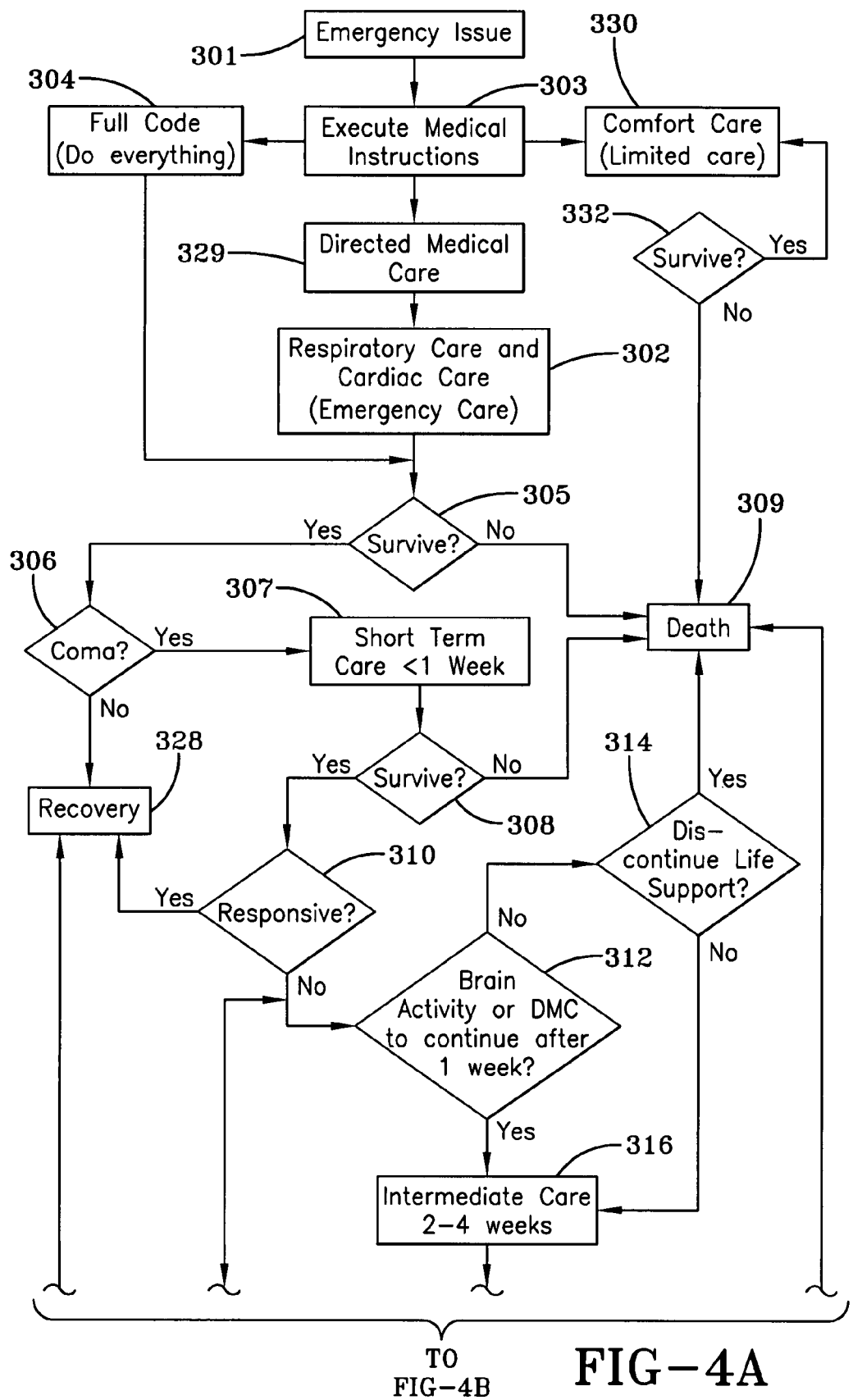
FIG. 4 is a flow chart illustrating the method for executing the created medical care instructions according to the present invention.
Figure 4B:
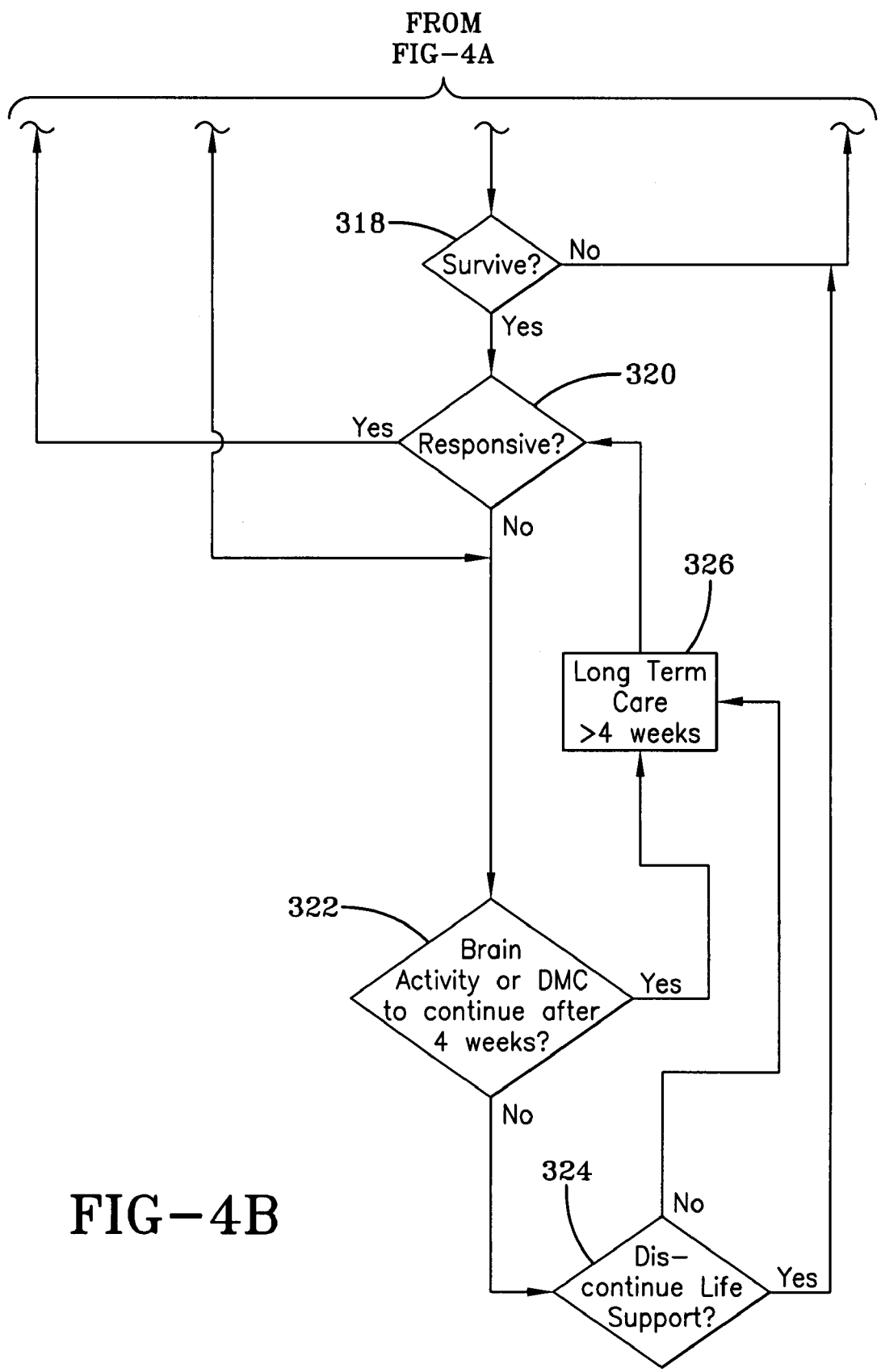

FIG. 4 is an exemplary flowchart illustrating the process for guiding an individual through the process of making end-of-life decisions.

Referring now to FIG. 4 and assuming the case of an expected emergency issue for an individual at step 301, the individual or initiates the process of creating medical care directives and at step 303 emergency medical personnel will access the patients accessible "directed medical care" information and will institute the directed medical care information at the start of providing medical care. Prior to the medical emergency occurring, when preparing the medical instructions and making his or her decisions, the individual selects the desired level of medical care for himself or herself, which can be "full code" (step 304), "directed medical care" (step 329) or "comfort care" (step 330). As shown in FIG. 7 which is an exemplary initial option chart, the individual will first be presented with these three options, i.e., full code, directed medical care and comfort care. Each option is provided with, for example, a hyperlink, to provide the individual with a definition of each selection and the details which pertain to each selection. The definition or other educational information may be shown in a new Internet website window, may be provided in a supplemental "pop-up" window or in a subsequent "page" when the system 100 is provided on an interactive CD or DVD.

It should be understood that a hyperlink is a navigational link from one document, such as an electronic or digital document, to another, from one portion (or component) of a document to another, or to an Internet web resource, such as a Java applet. Typically, the hyperlink is displayed as a highlighted word or phrase that can be selected by clicking on it using a mouse to be directed to the associated document or document portion or to retrieve a particular resource, such as via a downloadable component. The collection of hyperlink information of the present system is provided in a hypertext system, which is a computer-based informational system in which documents (or other types of data entities) are linked together via the hyperlinks to form a user-navigable "web." The information provided via the hyperlink may be stored, for example, in a content server or content database. The information may be stored as a text file described in a markup language typified by hypertext markup language (html), an audio clip/file, a picture/graphic file or a video clip/file.

Full code 304 indicates that the patient wants everything done to try to save his or her life. In other words, no decisions are to be made by the individual, but rather the patient desires that all measures be taken to save his or her life, including cardiopulmonary care, intubation, application of a ventilator (breathing machine), defibrillation (shocking), chest compressions, etc. This selection is typically made for all healthy, young to middle-aged people. The reason is that such a person is not expected to end up in the hospital, and so whatever happened to result in him or her being hospitalized was unexpected, (such as trauma, heart attack, asthma, stroke, pneumonia etc.) and the person and his or her family would like every measure possible to try to save him or her.

Elderly people may of course also select this option. However, as people age many of them prefer controlling his or her care and do not always desire all that which is provided with the "full code" choice.

The selection of step 329 (directed medical care) will be explained in detail below.

As should be appreciated by those of ordinary skill in the art, a majority of elderly people have given some thought to life threatening or life ending medical emergencies and have an idea of what they do and do not want done to them.

As can be seen during the initial care being a "full code 304," there are no choices to be made. As noted above, the patient receives any possible treatment for saving his or her life. However, there is still a need to guide health care providers with a level of care for the patient if he or she requires emergency care and/or long term treatment and is still unable to express his or her wishes. This is done at step 305 when the individual has provided directed medical care 329.

Figure 8A:
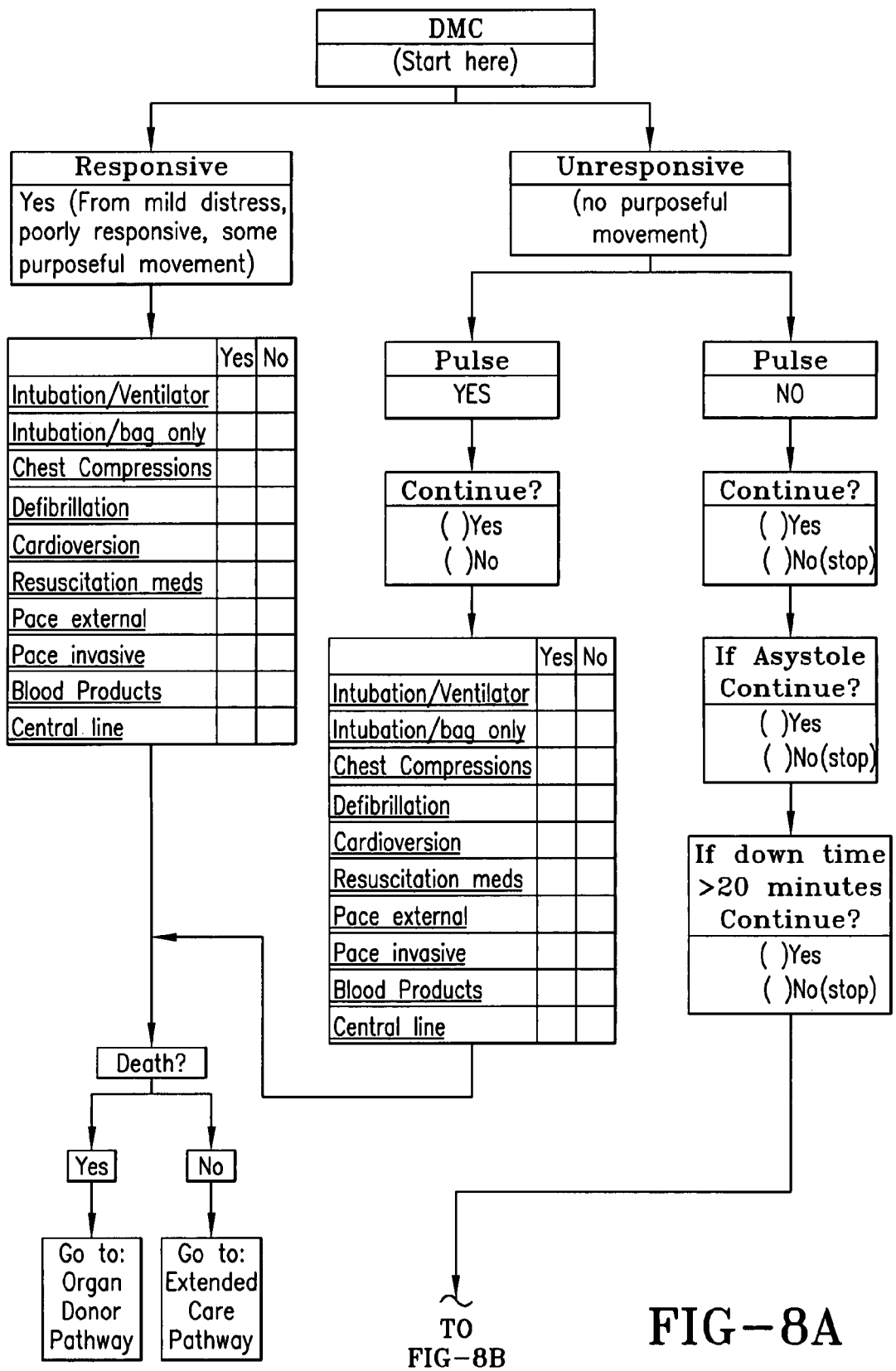
FIG. 8 is an exemplary selection chart providing possible treatment selections for a patient having directed medical care in an emergency situation.
Figure 8B:
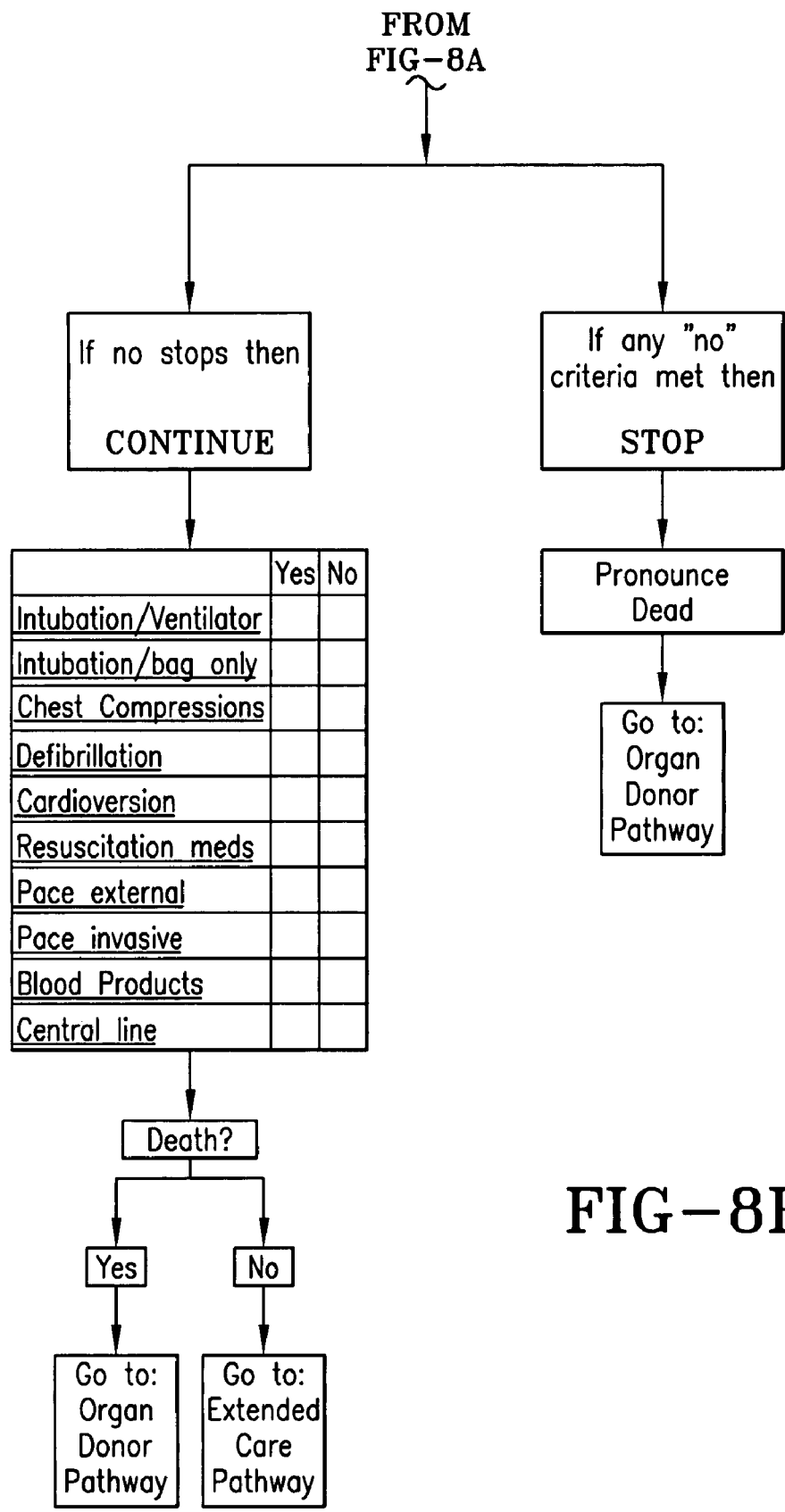

Upon selection of directed medical care 329, the individual may initially select between two scenarios where emergency care is required: (1) the individual is responsive, and (2) the individual is non-responsive. In the case where an individual is responsive, the individual selects which treatments he or she desires to be administered during an emergency situation. FIG. 8 is representative of a set of possible treatment options which an individual may select in an emergency situation, each option being provided, for example, in a hyperlink form for providing additional information to educate the individual about the particular selection. In the case where an individual is non-responsive, the individual selects which treatments he or she desires to be administered during an emergency situation which are the same treatment options provided in the chart of FIG. 8. If an individual is unresponsive, an individual may select, for example, whether he or she does or does not wish treatment to be administered in the event a pulse is detected or not. If a pulse is not detected, an individual may elect, for example, whether he or she does or does not wish treatment to be administered in the event that an asystolic condition is determined, and if so, whether treatment should continue if the asystolic condition lasts for more than a given amount of time (such as for more than 20 minutes). In other words, the individual has the ability to determine the exact moment when administration of medical treatment should be discontinued and the amount of time for which treatment should be provided.

When the individual initially survives an emergency, the survival result may be a coma at step 306. The event of the patient not surviving at step 305 results in death at step 309. If there is no coma and the patient recovers at step 328, the procedure terminates at step 328 (recovery) and the patient is discharged, or possibly enter post-treatment therapy/rehabilitation. In the case of a coma at step 306, short term care of less than one week is provided at step 307 and the individual must provide directives for short-term medical care. Short term care at step 307 includes various types of treatment and procedures, for example, respiratory care, cardiac care, hydration and other medical interventions to prolong and improve life by treating the underlying medical condition. Respiratory care deals with improving one's ability to breathe, which may only require oxygen, airway suction, or breathing treatments. These are considered basic necessities and noninvasive, thus they should be basic care to everybody. However, some individuals may require a definitive airway by intubation, leading to placement of the person onto a "breathing machine" (ventilator). All other respiratory care is usually not an issue. Intubation is the placement of a tube into one's wind pipe to administer oxygen. The tube is then connected to a breathing machine (ventilator). The individual is typically sedated during this process, while increasing oxygen to the organs maximizes the patient's chances of recovery. The tube may then be removed once the body has recovered. This process can take as little as a few days; however, the person may never recover enough to be removed from the ventilator. Virtually nobody wants to be on a ventilator forever, but there are instances where ventilation can be beneficial for short periods of time. The directed medical care document according to the present invention was designed to give the patient control over the length of time spent on the ventilator (or other medical treatment) while the patient's body tries to recover from the traumatic event. FIG. 9 sets forth a selection chart with each possible potential option available to the individual during short-term critical care 307. Each option is provided with a hyperlink, for example to provide additional information on that selection to educate the individual. The patient may wish to obtain additional information regarding any particular option in order to make a proper selection. By clicking the hyperlink for a particular option, the individual is directed to the corresponding information database, such as an educational demonstrative video link, as shown in FIG. 9.

The patient may not survive at step 308 after short term care at step 307, thereby resulting in death at step 309 and terminating the procedure. In the event of the patient's survival at step 308 and the patient being responsive at step 310, he or she recovers at step 328, at which step the procedure then terminates. A typical problematic scenario in the current art is that an elderly patient with a living will states that he or she does not want to be on a breathing machine, which is understandable. However, there are situations where this choice could prematurely end the patient's life. By choosing "intubation and the breathing machine" for a short period of time, the patient could recover and potentially be provided with many more years of quality time with family and loved ones. If one chooses not to be intubated and on the ventilator, there is a high likelihood he or she could die from this traumatic event. The downside of choosing to be intubated is that one might not recover, will not be able to be removed from the breathing machine and will ultimately become dependant on the ventilator. This is what most would want to avoid. There are some situations where one is in distress but conscious. Therefore, if the outcome is what one does not want, then he or she can still be in charge of his or her care when using the system of the present invention.

When preparing the medical care instructions, one can limit the time that is designated as "time to recover" in the event the patient is non-responsive at step 310. This limits what most people fear, namely, being on the "breathing machine" forever. This step thus allows the individual to choose whether to stop the aggressive medical care before it starts (step 302), after a short attempt at resuscitation (step 305), or after short term care (step 312), intermediate care (step 322) or anytime during long term care (step 326). At step 312, aggressive medical care has been extended for over 1 week. At this point, the brain wave activity will be reassessed if the patient has not recovered. The patient would have the option of selecting whether treatment should be continued if no brain wave activity is found, continuing on to intermediate-term medical care 316, or whether treatment should be discontinued to allow death to occur. In other words, the individual has a choice (or has previously made the choice, which is incorporated in the system as an electronic instruction) of either discontinuing life support at step 314, which would lead to death at step 309, or proceeding to step 316 which offers intermediate term care (i.e., 2-4 weeks).

While preparing the medical directives, the individual again is presented with the selection chart of FIG. 9 to select the desired medical treatment to be administered during intermediate-term medical care 316. In a fortunate event of surviving at step 318 and being responsive at step 320, the individual will recover at step 328, where the procedure terminates. Not surviving at step 318 leads to death at step 309, where the procedure terminates. In the event of not being responsive at step 320, when preparing the medical care instructions, one again has chosen on whether continuing treatment, such as respiratory care and cardiac care (step 322), which results in long-term care for over four weeks at step 326. While preparing the medical directives for long-term care, the individual again is presented with the selection chart of FIG. 9 to select the desired medical treatment to be administered during long-term medical care 316. At this point, one can also make a decision to proceed to step 324, i.e. to discontinue life support. Obviously, discontinuing life support leads to death at step 309, where the process terminates, or alternatively proceeds to the organ donation process. In the event the individual makes a decision not to discontinue life support, flow proceeds to step 326 for long term care. As it is seen from the flowchart in FIG. 4, step 322 may be chosen also at step 310. Steps 307, 316, and 326 include, without limitation, the choice of a ventilator, feeding tube, dialysis, surgical airway, diagnostic studies and treatment of the underlying medical condition, etc., as well as any combination thereof.

Figure 9B:
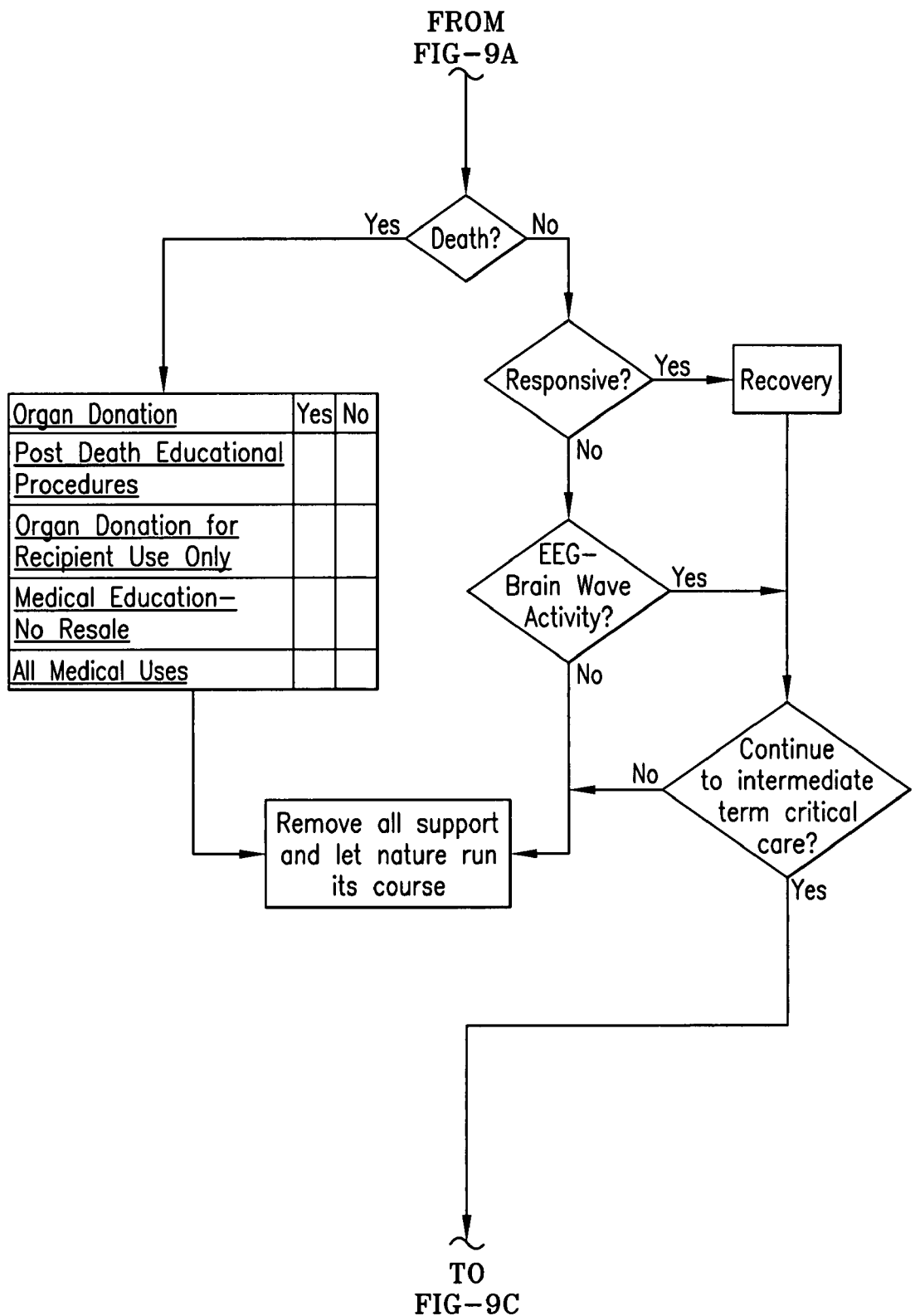
FIG. 9 is an exemplary selection chart providing end-of-life selections for a patient having directed medical care for an extended amount of time.
Figure 9C:
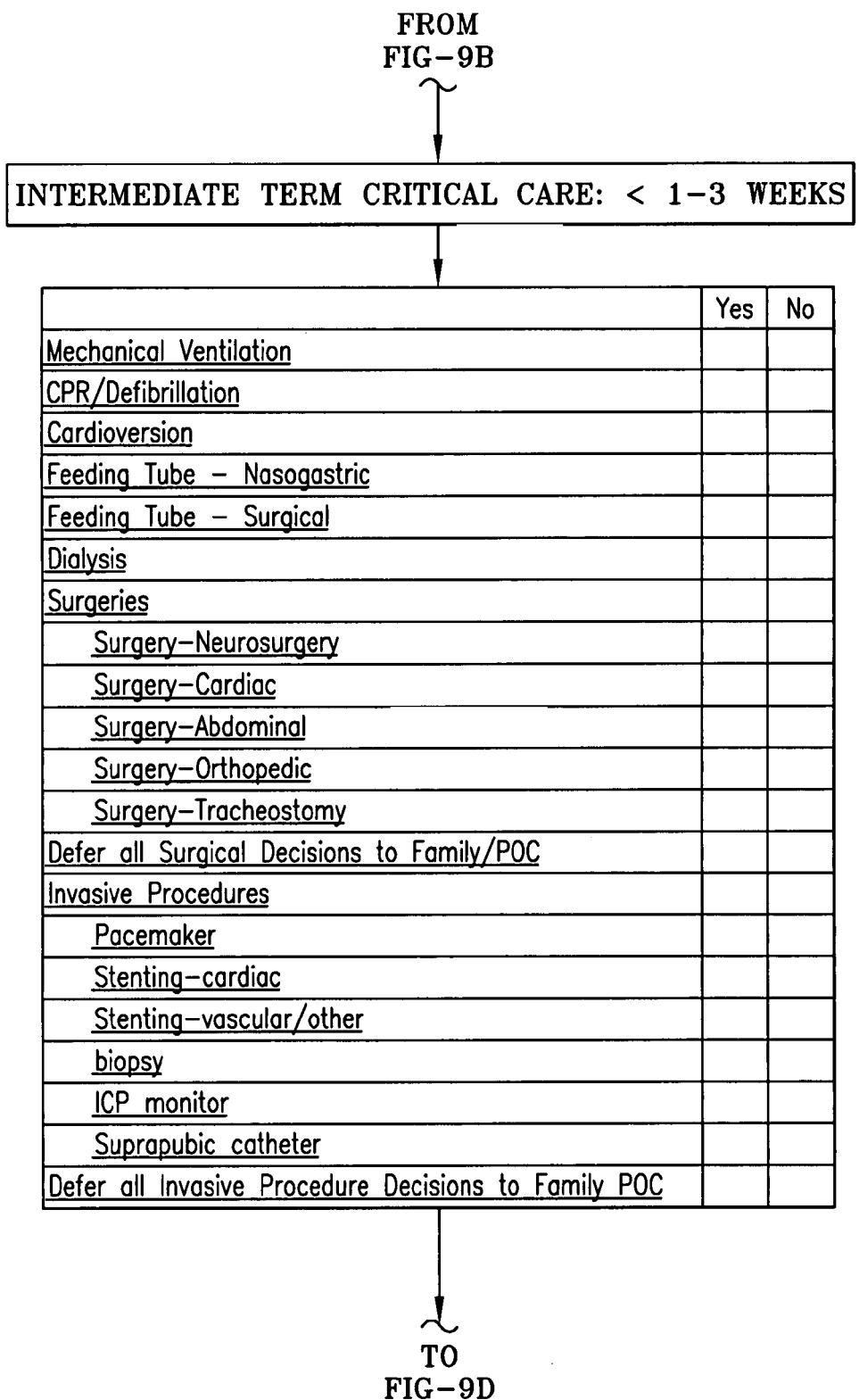
Figure 9D:
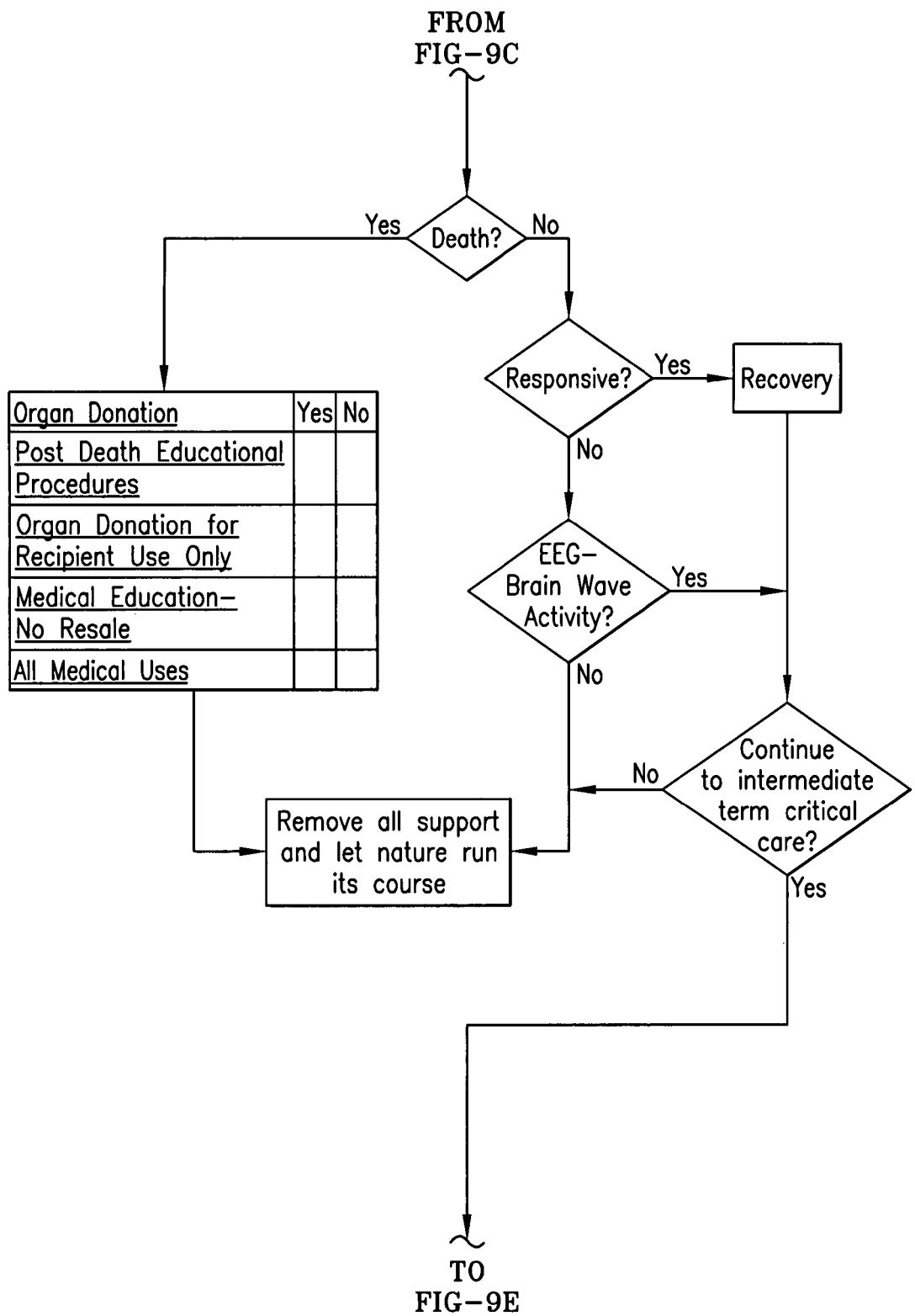
Figure 9E:
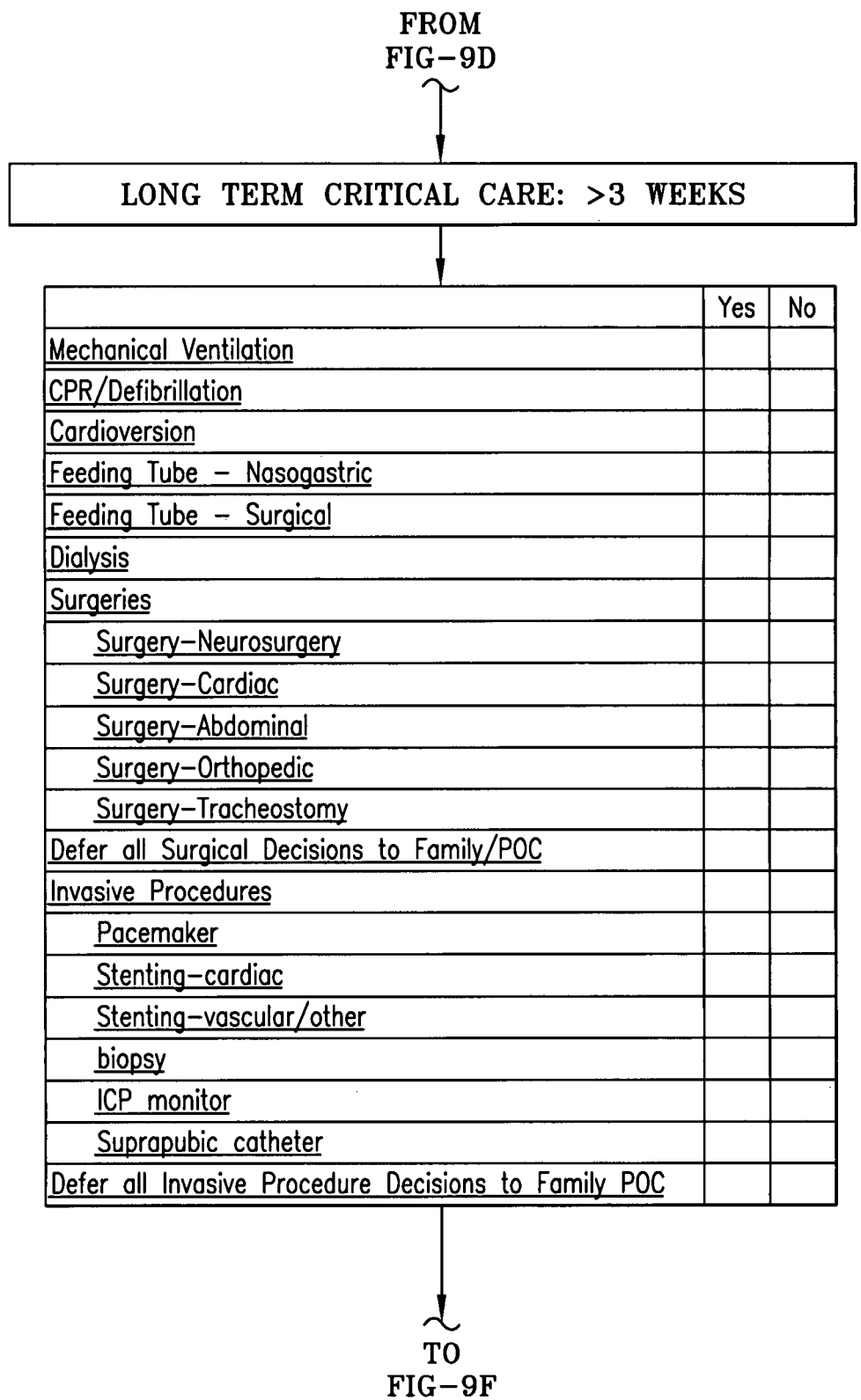
Figures 9F, 10:
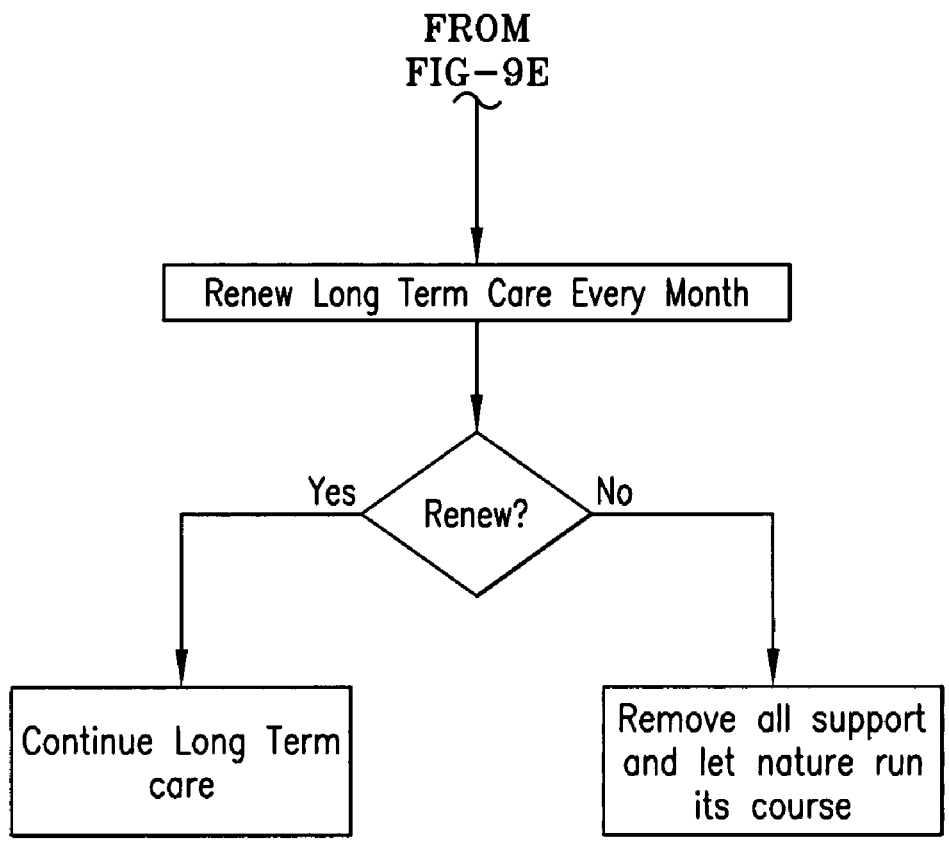
FIG. 10 is an exemplary selection chart providing post-death organ donation selections for a patient.

The individual is ultimately presented with a final option which pertains to post-death directives, i.e., whether organ donation is desired, and if so, for what purpose. FIG. 10 sets forth an exemplary selection chart addressing post-death organ donation. For example, an individual may choose that no organ donation should be done, that organ donation is acceptable for only post-death education procedures, for organ donation for direct recipient use only, organ donation for medical education only (i.e., no resale) or organ donation for all medical uses. Each option is provided in a hypertext (or hyperlink) format for providing additional information for explaining the details of each option to the individual.

Step 330 deals with "comfort care". This choice is often times made by one holding Power of Attorney or family members directly in charge of the patient's care; however the individual may pre-select which comfort care measures are to be provided in anticipation of death. It would be unusual to select comfort care if one is still making his or her own decisions. If one is still making his or her own decisions, usually he or she would select one of the choices above, such as "full code" (step 304), directed medical care (step 329), "short term care" (step 307), "intermediate term care" (step 316), or "long term care (step 326)".

Choosing step 330 may indicate that death is imminent in view of a particular set of emergency circumstances. Therefore, if an emergency situation occurs, the patient/patient's family understands that this medical emergency may cause the patient's demise and that the patient would like the process of dying to be as painless as possible. Most family members choose this because the individual has told them in the past that he or she would not want to live in a semi-vegetative state, in a bed ridden condition or on a breathing machine. If one chooses this option, provisions will be in the form of comfort measures only. Comfort measures may include, for example, pain control, fluids, splinting, oxygen and airway suction if needed. This decision could have been made previously by the individual, who would have previously selected an appropriate directive in the system. In other words, the patient could have previously elected that only comfort measures may be provided if and when a particular medical emergency (or emergencies) arises. It should be appreciated that the individual may select comfort care 330 for only certain limited situations, directed medical care 329 for additional situations and also full code 304 in yet additional certain situations. FIG. 11 is an exemplary selection chart for possible comfort care medical instructions, which may include without limitation, any optional measures in addition to those which are always provided, any possible surgical options, such as tracheostomy, any possible "cost-saving" options which are often times unnecessarily administered by medical personnel, such as endoscopy/colonoscopy. Organ donation options may also be provided, as discussed above. Each option is provided in a hypertext format for providing additional information to the individual by way of video files, picture files and the like.

With reference to FIG. 12, an example of output directed medical care information 208/medical instructions 303 is set forth for use with comfort care (step 330). When preparing the medical care instructions, the patient selects (1) in which situations or medical emergencies the patient prefers that no treatment be provided, except for standard comfort care measures, and (2) which additional comfort care measures are to be provided by the medical team. It is of course appreciated that the standard comfort care measures are to always be provided regardless of which additional measures the patient desires. Comfort measures which should always be provided to a patient having chosen comfort care (step 330) may include provisions for pain management, providing oxygen and suction in the least invasive manner possible, splinting of fractured bones, repair of lacerations, the checking, correcting and maintenance of low blood sugar and the positioning of the patient's body to maximize comfort and to eliminate or at least reduce the chance of obtaining bed sores. The patient having selected comfort care 330 will then have pre-selected which of any number of "optional" provisions may or may not be provided, which surgeries may or may not be provided and which of any number of "extra" provisions which generally are not part of comfort care, but may or may not be provided. Additionally, the comfort care patient would have the opportunity by way of the present system to have pre-determined whether or not his or her organs are available for donation if he or she passes away. If the patient chooses to allow organ donation, he or she would further be able to select from any number of situations for which his or her organs may be donated, e.g., solely for post death educational procedures, medical education only (no resale of organs) or for all medical uses.

Comfort care at step 330 is continued for as long as the patient survives, or until death occurs at step 309. Also illustrated in FIG. 3 is an example of questions which may be included in a form stored in the forms database 220, as described in detail above.

Figure 5:
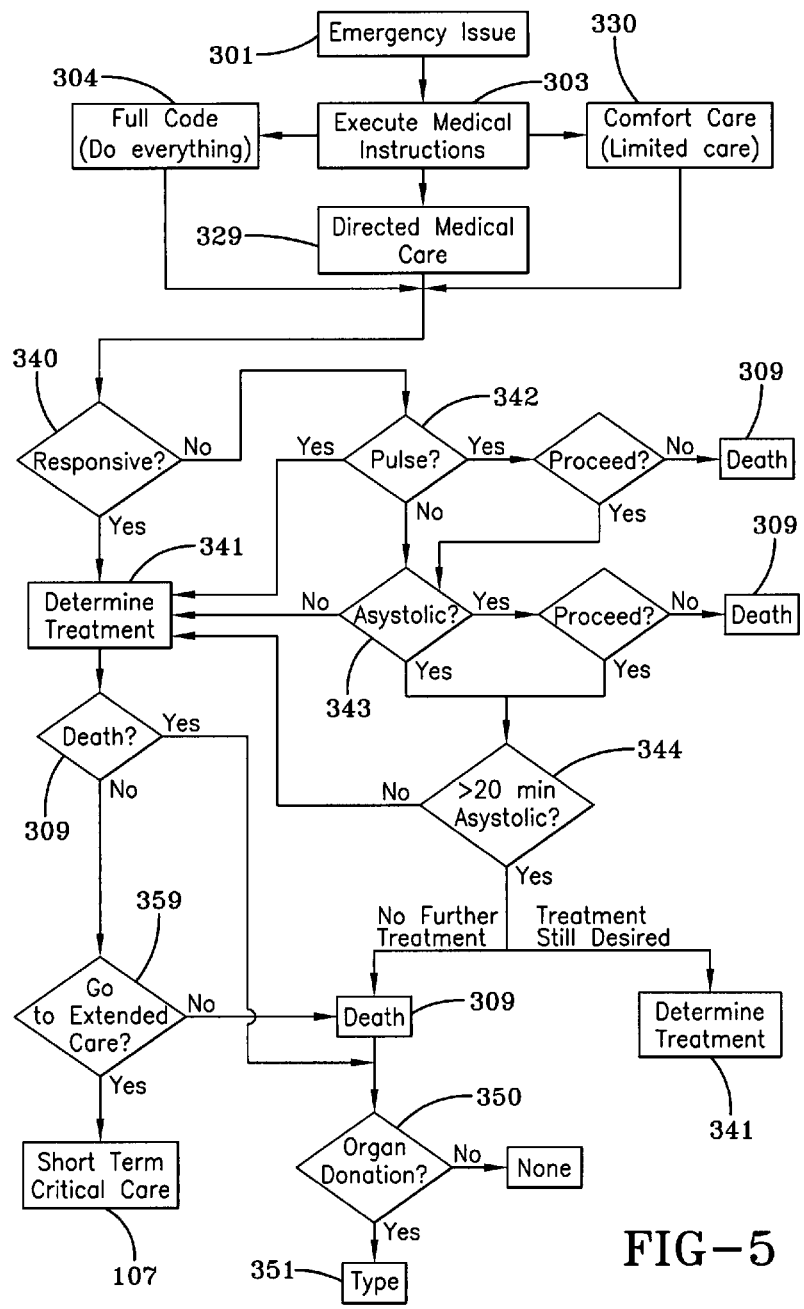
FIG. 5 is a flow chart generally illustrating a method for executing emergency medical care in accordance with a patient's created medical care instructions.

Turning now to FIG. 5, a general example of an output directed medical care information process for guiding a medical team through the process of end-of-life decisions as directed by a patient is shown and described. An emergency issue for an individual occurs at step 301 and the individual or family will activate an emergency medical team (i.e., 911) or proceed to the nearest emergency room, where at step 303 emergency medical personnel will immediately access the patient's up-to-date "directed medical care" information, such as by way of a direct, secure connection with the Internet website central database, cellular phone transmission, radio transmission, a CD, a DVD, a USB card, fingerprint recognition and the like, and will institute the proper care upon initiation of medical care. As also the case with the process set forth in FIG. 4, prior to the medical emergency, when preparing the medical instructions and making his or her decisions, the individual selects the desired level of medical care for himself or herself insofar as any particular medical emergency is concerned, which can be "full code" (step 304), "directed medical care" (step 329) or "comfort care" (step 330). The output directed medical care information will explicitly set forth this selection at the onset and the medical team will quickly be able to determine the level of care which is to be given in response to the particular medical emergency at hand.

The medical team quickly accesses and reviews the individual's medical decisions and proceeds according to the individual's instructions, i.e., comfort care, directed medical care or full code. If comfort care 330 has been selected, the medical team refers to the outputted comfort care chart (FIG. 12) and proceeds accordingly. If full code 304 has been selected, the medical team administers all possible treatments to the patient. If the individual has selected directed medical care 329, the medical team proceeds according to the individual's pre-selected instructions. Once the particular level of medical care for the patient is ascertained by the medical team, the team determines whether the patient is responsive at step 340. Typically, a patient is considered to be responsive if he or she suffers anywhere from mild distress to being poorly responsive, i.e., the patient has at least some purposeful/intentional movement. If the patient is responsive, the medical team determines which type(s) of treatment are to be applied by referring to the particular patient's treatment chart as provided in the output directed medical care information (FIG. 8). The treatment chart explicitly states whether or not any number of possible treatments may be provided when the patient is responsive, such as intubation, application of a bag valve mask, ventilation, application of an external pacemaker, application of an invasive or external pacemaker, application of blood products, application of a central IV line, chest compression, defibrillation, cardioversion (a brief procedure where an electrical shock is delivered to the heart to convert an abnormal heart rhythm back to a normal rhythm) or resuscitation medications. The particular treatment(s) set forth in the patient's treatment chart (FIG. 7) is predetermined by the patient and is dependent upon the level of medical care selected by the patient.

Figure 13A:
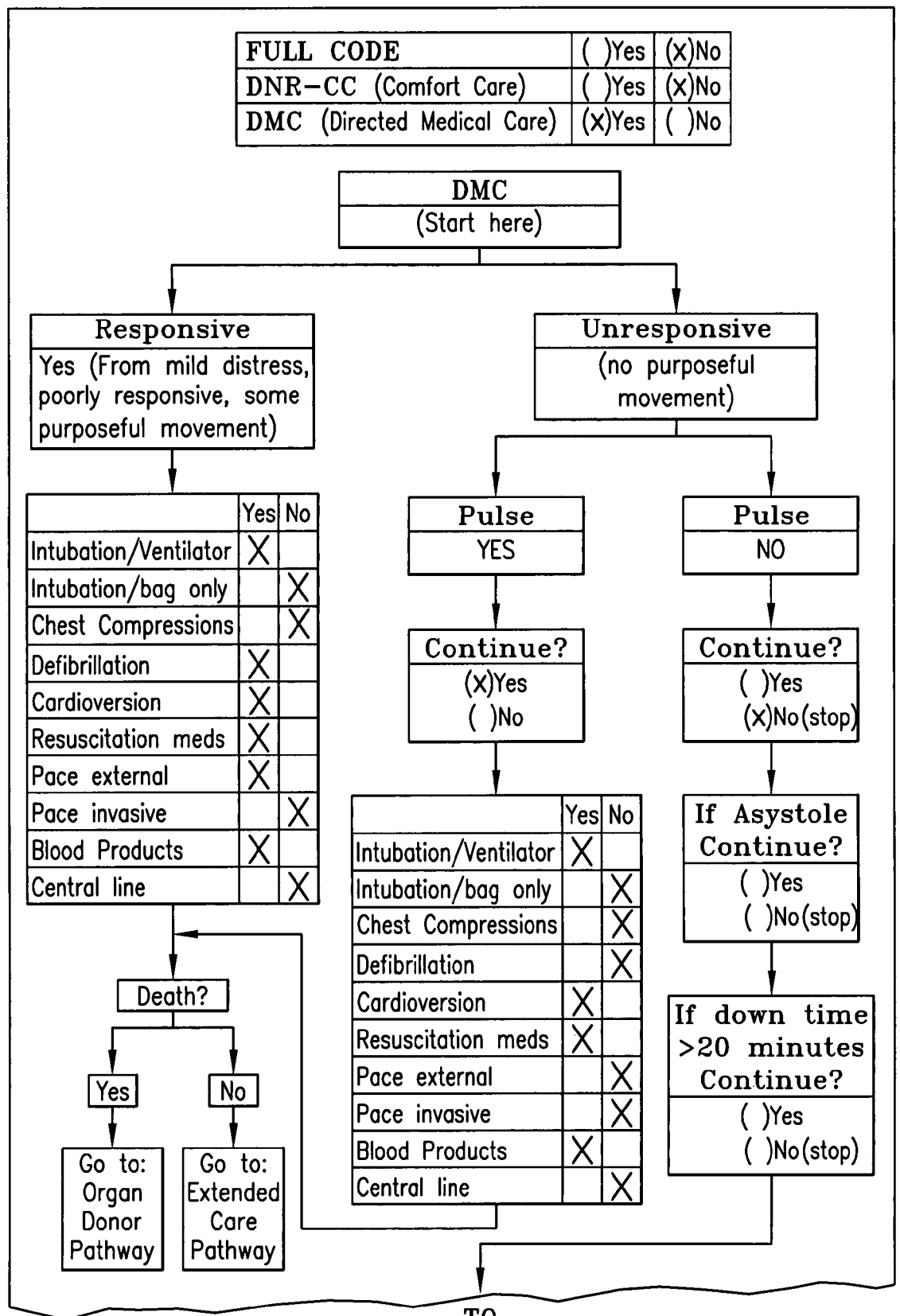
FIG. 13 is an exemplary output chart providing end-of-life selections for a patient having directed medical care in an emergency situation.
Figure 13B:
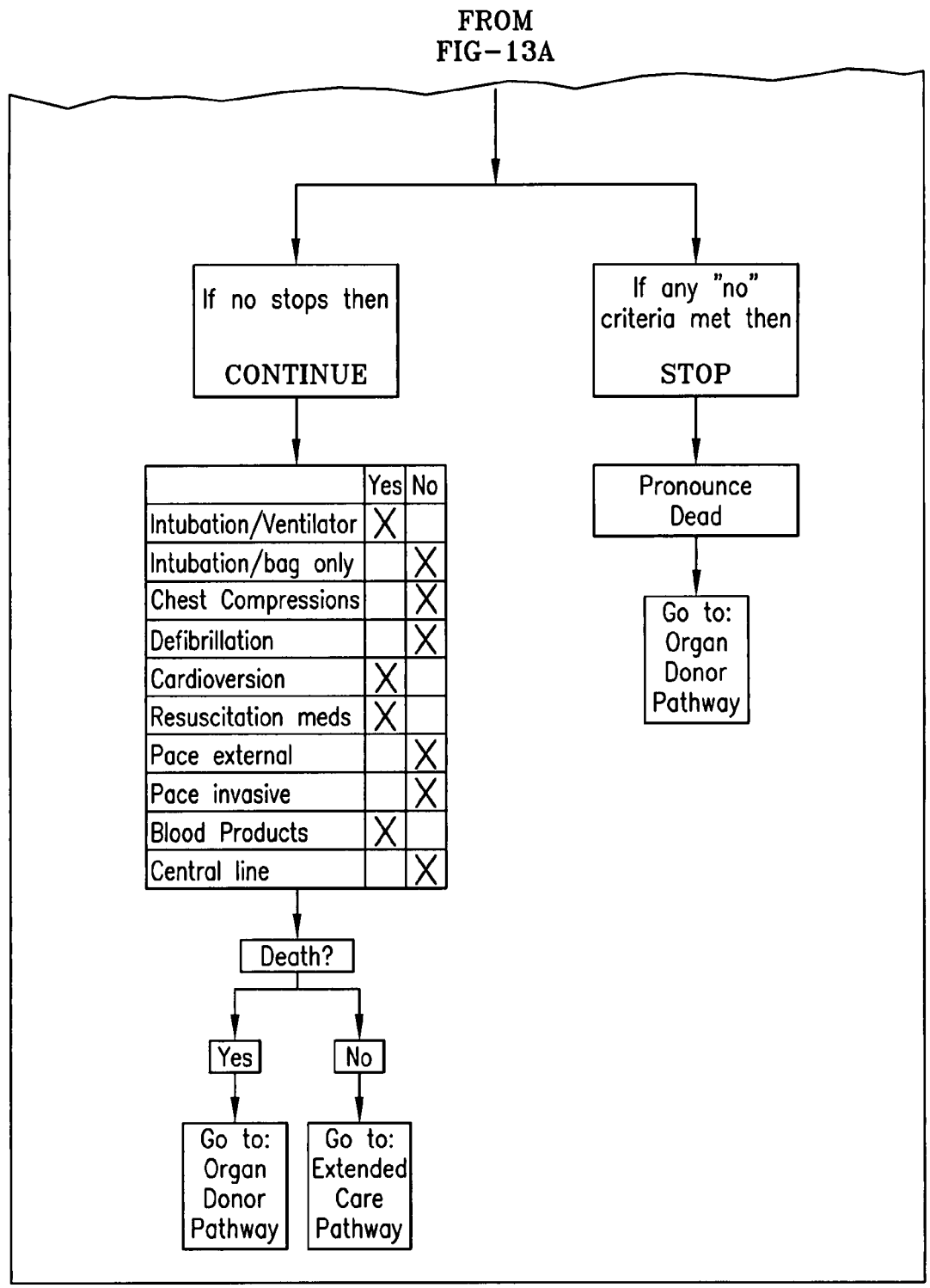
Figure 14B:
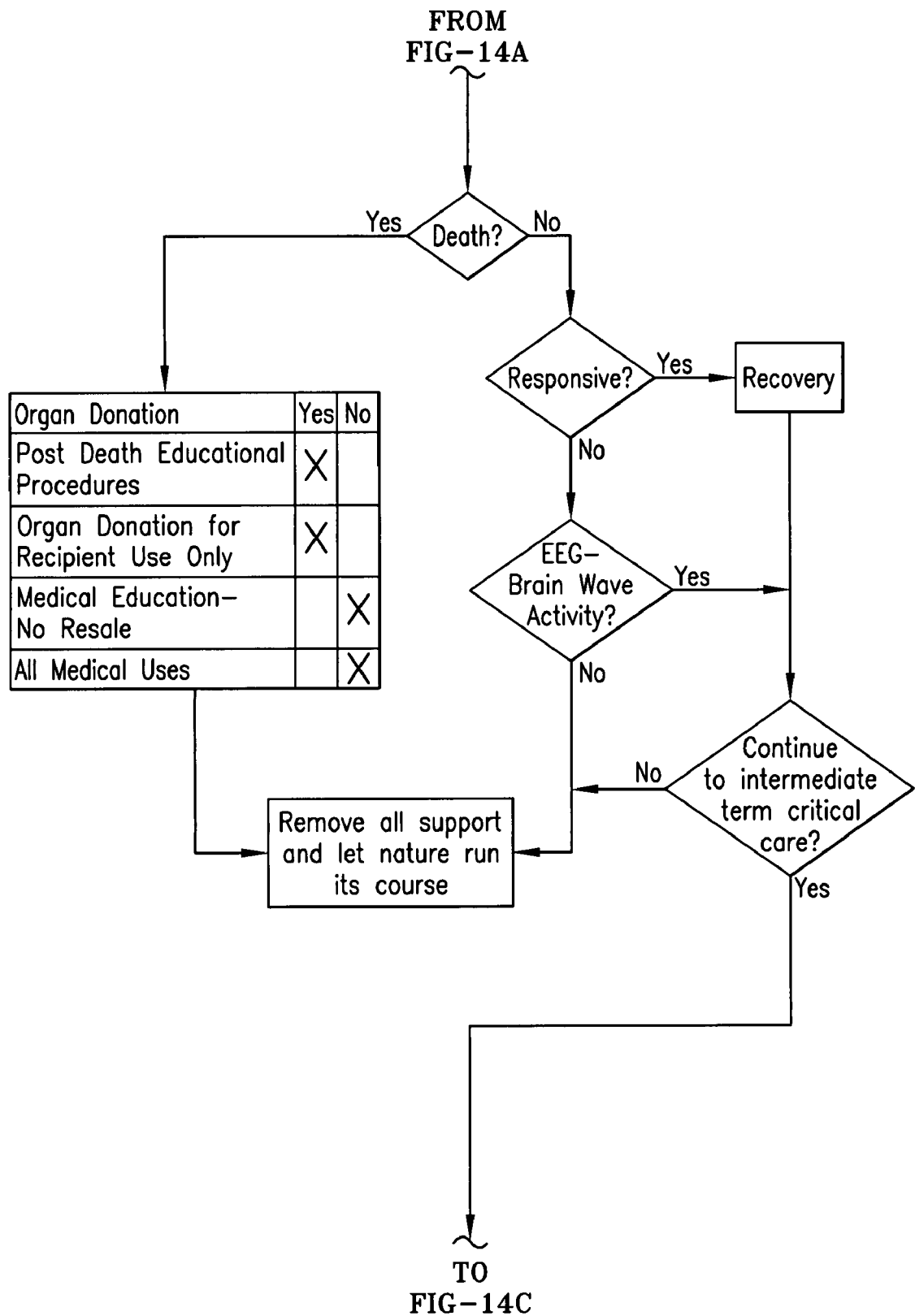
FIG. 14 is an exemplary output chart providing end-of-life selections for a patient having directed medical care for an extended amount of time.
Figure 14D:
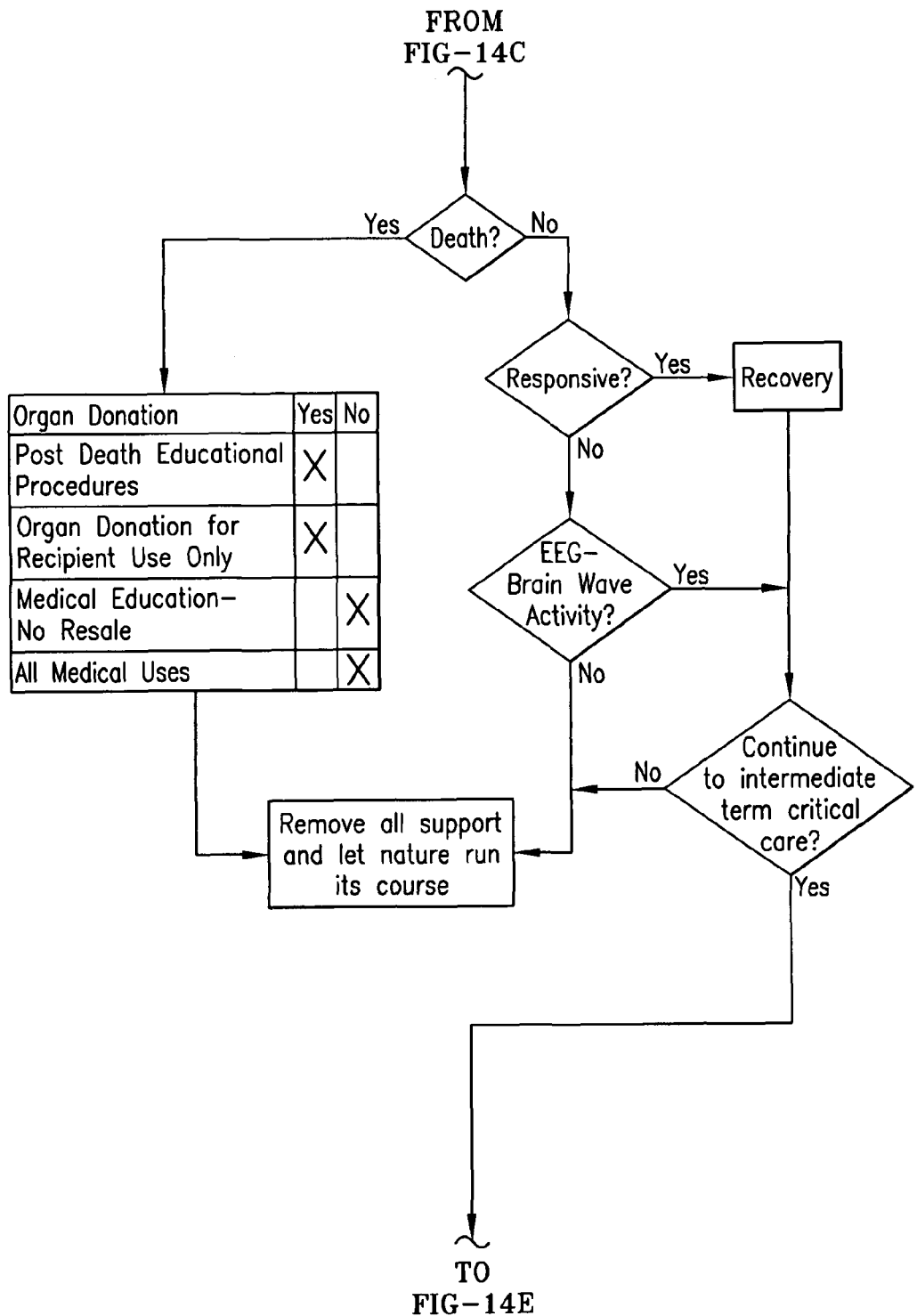
Figure 14E:
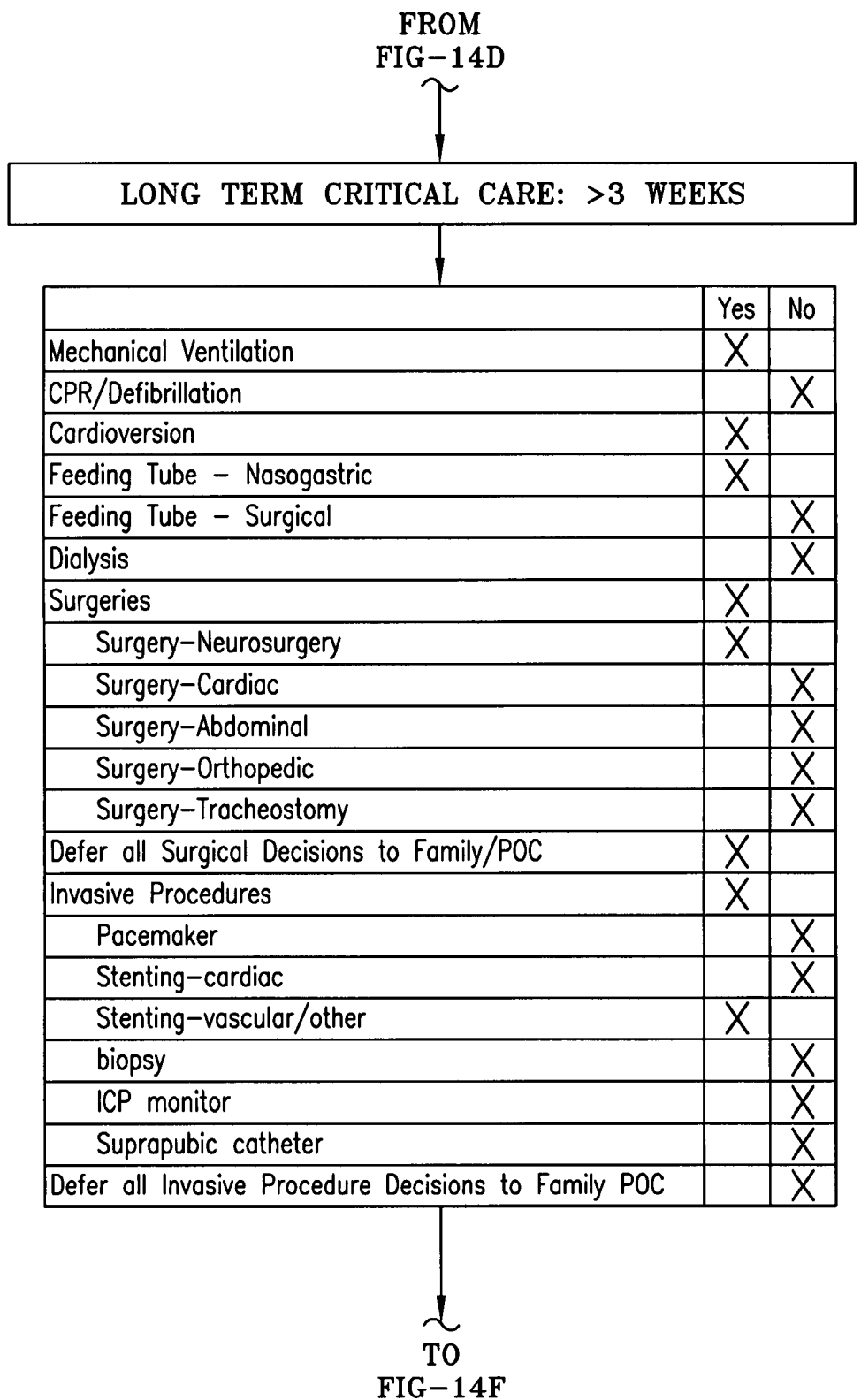
Figure 14F:
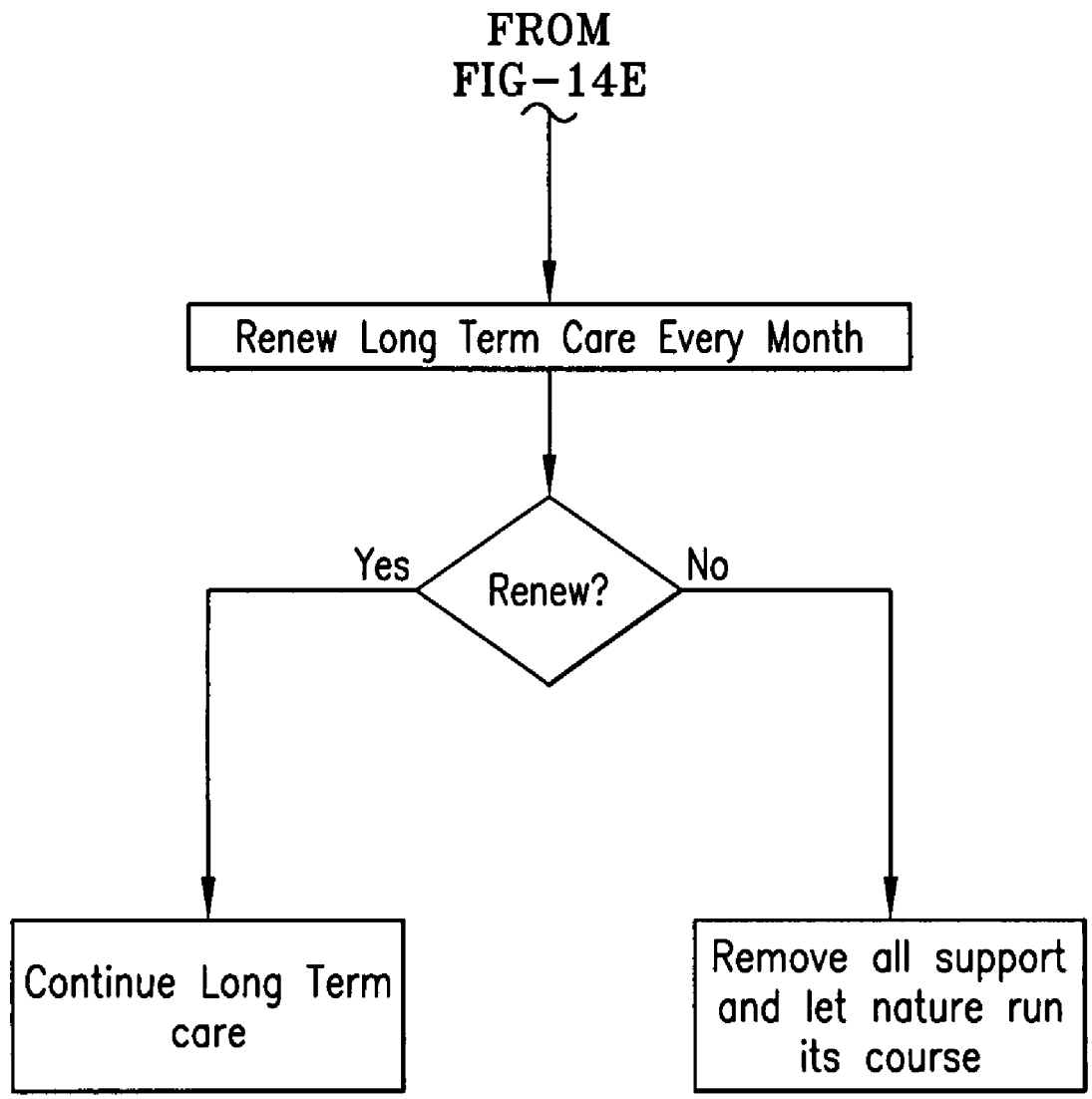

Still referring to FIG. 5, if it is determined that the patient is unresponsive at step 340, then the medical team checks the patient's pulse at step 342. If the patient has a pulse, then the applicable treatment(s) as instructed by the individual in the outputted emergency care chart (FIG. 13) is determined at step 341. It should be appreciated that the individual may have selected "no treatment" in the event that the individual is unresponsive at step 340, in which case death arise at step 309 arises and the process proceeds to the organ donation step 350. If the patient has a pulse at step 342 and has instructed treatment at step 341, then the medical team administers treatment accordingly. Successful treatment results in recovery; unsuccessful treatment results in death 309 or a determination of proceeding to extended care at step 359. If the individual has instructed not to proceed to extended care, then death arises at step 309.

If the patient has no pulse at step 342, the medical team subsequently first ascertains whether to proceed. If the directives state not to proceed, then death arises at step 309. If the medical team may proceed, then a determination is made as to whether the patient is asystolic (i.e., has no cardiac electrical activity) at step 343. The medical team proceeds to step 341 to determine the correct treatment(s) (FIG. 13) for the patient if the patient is not asystolic and wishes treatment to be administered. If it is determined at step 343 that the patient is asystolic, then the medical team may proceed to step 344 (unless the directives instruct not to proceed further) where it is ascertained whether the asystolic condition has been occurring for more than a provided amount of time, i.e., 20 minutes. The subsequent treatment(s) (FIG. 13) provided to the patient at step 341 is now dependent on whether the patient is or is not asystolic. It is possible that the patient may have predetermined that no treatment be provided if the asystolic condition has occurred for more than 20 minutes, in which case death would arise at step 309.

Once death has occurred, the medical team may refer to the patient's selection as to whether any organ donation is to occur at step 350. If it is determined that organ donation is to occur, then it must be determined (step 351) what type of donation may occur and for what purpose. FIG. 10 represents the organ donation chart which sets forth any number of possible organ donation conditions which a patient may have selected. For example, the patient's desires may be to allow organ donation for post-death educational procedures, for medical education only (i.e., no resale) or for all medical uses.

Figure 6A:
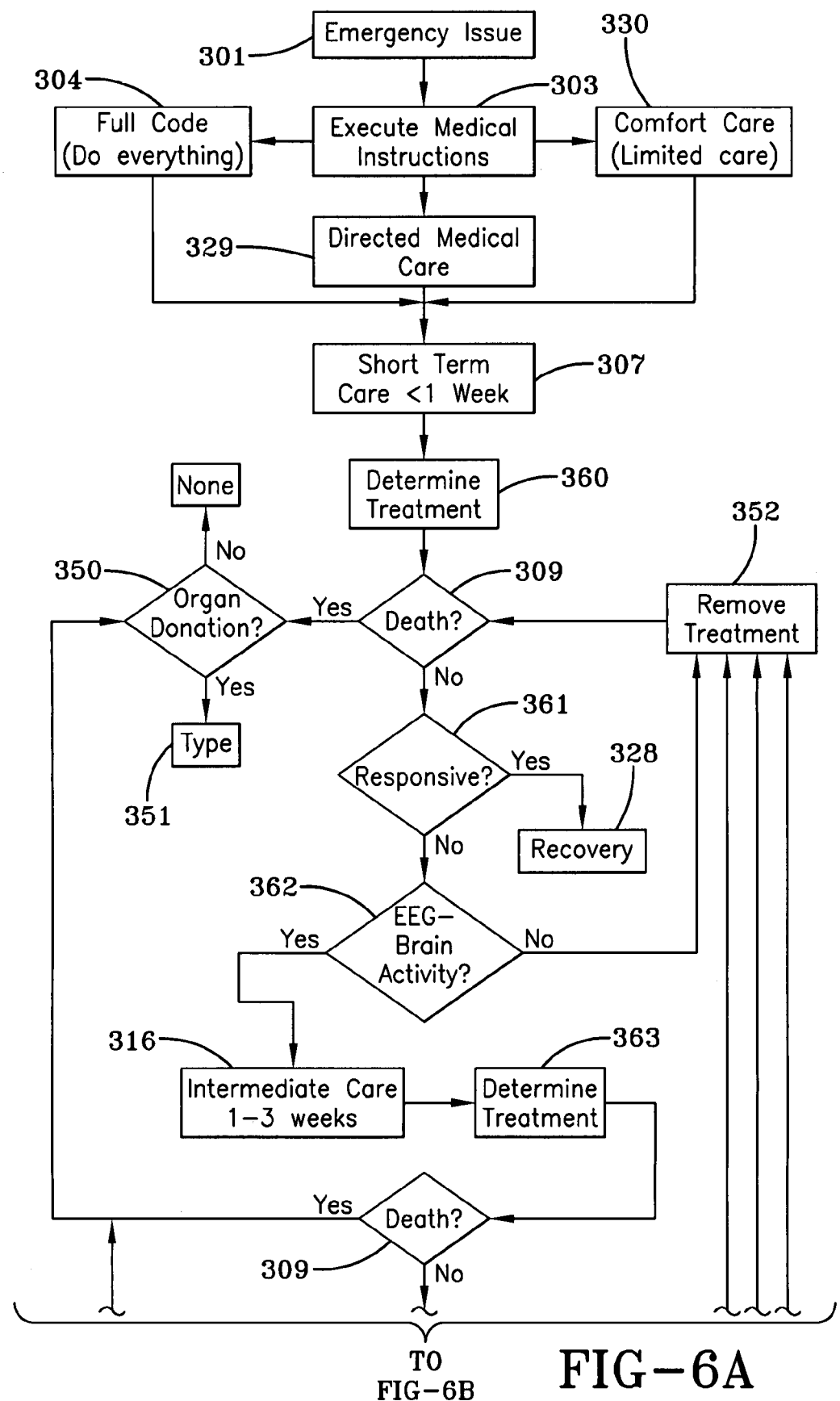
FIG. 6 is a flow chart illustrating a method for executing directed medical care information in accordance with a patient's desires according to the present invention in the case when an emergency issue requiring extended medical care has arisen.
Figure 6B:
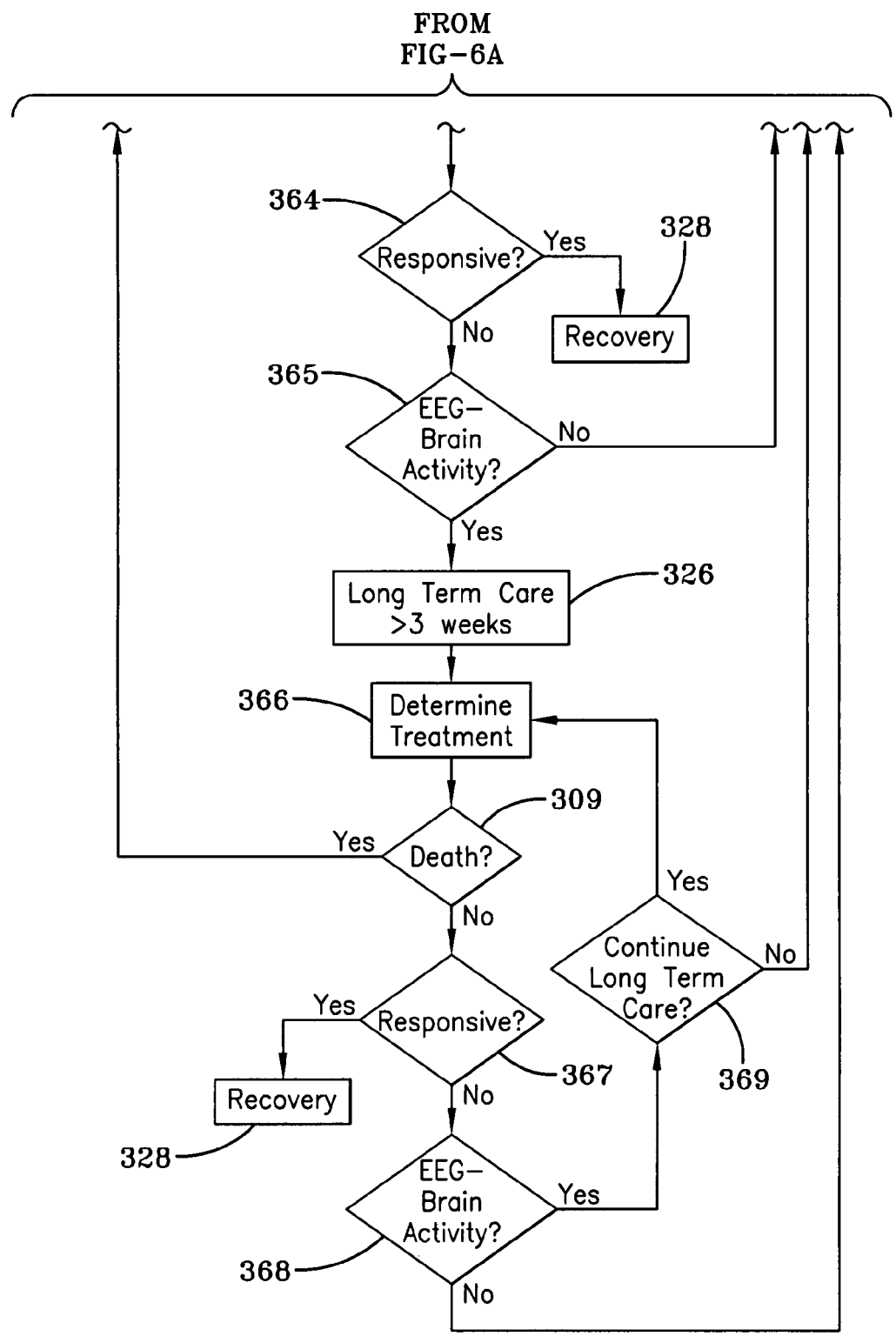

Turning now to FIG. 6, the process of providing medical care instructions in an extended care situation according to the present invention is illustrated by way of a flow chart. It should be appreciated that the individual has already selected specific medical care directives by way of the present invention in the case of an emergency situation, the directives being accessible by a medical team by way of, for example, a secure Internet central database, a chip kept on the individual, fingerprint recognition, etc. As noted above, an emergency issue arises at step 301 requiring the individual to be transported to a hospital or other medical facility whereby a medical team reviews and executes the patient's particular pre-selected emergency medical instructions at step 303. In other words, the medical team has determined at step 303 whether the patient requires full code treatment (step 304), directed medical care (step 329) or comfort care (step 330). Any number of treatments may subsequently arise as a result of the particular level of care selected by the patient, as discussed below. In this instance, the patient has selected directed medical care at step 329 and has made the determination that extended care is to be provided at step 359 (FIG. 5).

As shown in FIG. 6, once the level of care is determined at step 303, the treatment(s) which are subsequently applicable to the patient must be determined and applied. In the example set forth in FIG. 6, it is shown that short-term care is initially required and the present example will begin accordingly.

At step 307, short-term critical care is selected for the patient in an emergency situation. Short-term critical care 307 is generally defined by critical care treatment lasting for less than one week. Subsequently, the type of treatment(s) is determined at step 360. Any number of treatments may be selected, as specified on the selection chart depicted in FIG. 14. As shown on the outputted extended care chart of FIG. 14, treatment types may include, but are not limited to, ventilation, application of a feeding tube (nasogastric or surgical), CPR/defibrillation, dialysis, surgeries, including, neurosurgery, cardiac, abdominal, orthopedic, tracheostomy (surgery selection may also be deferred to a medical proxy), or a variety of invasive procedures, such as application of a pacemaker, application of a cardiac stent, vascular stent, etc., biopsies, ICP monitoring, placement of a supra pubic catheter, or deferment of procedure decisions to a medical proxy. Once short-term critical care treatment is determined and administered accordingly at step 360, the medical team determines whether death has occurred at step 309. If death has occurred, then step 350 dictates whether the patient has authorized organ donation and any applicable types thereof (steps 350, 351), as discussed above with reference to the organ donation chart (FIG. 10). If death has not occurred, the medical team evaluates whether the patient has positively or negatively responded to treatment at step 361. If the patient has responded positively to the short-term critical care treatment 307, then the patient has recovered at step 328. If not, then the medical team evaluates whether the patient has EEG-brain activity at step 362. At this stage, the patient has selected whether or not he or she prefers additional treatment. For example, the patient may not desire additional treatment if no EEG-brain activity is present, in which case treatment is removed at step 352 and death arises at step 309. The medical team may proceed to the organ donation evaluation phase at step 350. Alternatively, the patient may desire additional treatment. In this case, treatment proceeds to intermediate critical care (step 316). Intermediate critical care is typically defined by medical care lasting in the range between 1-3 weeks.

Intermediate critical care is initiated at step 316. Subsequently, the medical team determines the type(s) of intermediate critical care treatment 316 required at step 363. Reference to the chart of FIG. 11, the output directed medical care information dictates the types of treatments which may be applied at intermediate critical care 316. It should be appreciated that the treatment(s) provided for intermediate critical care may be more restrictive than those provided at short-term critical care. Once treatment has been administered, the medical team determines whether death has occurred at step 309. If so, any potential organ donation is determined at steps 350, 351, as discussed above. If death has not occurred, the medical team evaluates whether the patient has responded to the intermediate care treatment at step 364. A positive response to treatment indicates the patient has recovered at step 328. A negative response to treatment indicates that the medical team must determine whether EEG-brain wave activity is present at step 365. As in the case of post-short-term critical care treatment, the patient has pre-selected whether he or she desires treatment to be removed if there has been no recovery and there is no EEG-brain activity, or whether additional treatment is desired. In the case of removal of treatment at step 352, death occurs at step 309. If additional treatment is required, then the medical team proceeds to long-term critical care treatment at step 326. Long-term critical care treatment is typically defined as treatment lasting for over three weeks.

Long-term critical care is initiated at step 326. Subsequently, the medical team determines the type(s) of long-term critical care treatment required at step 366. Reference to the chart at FIG. 14 dictates the types of treatments which may be applied for long-term critical care 326. It should be appreciated that the treatment(s) provided for long-term critical care may be even more restrictive than those provided at intermediate critical care. Once treatment(s) has been fully determined and administered, the medical team determines whether death has occurred at step 309. If so, any potential organ donation is determined at steps 350, 351. If death has not occurred, the medical team evaluates whether the patient has responded to the treatment at step 367. As in the cases above, a positive response to treatment indicates the patient has recovered at step 328. A negative response to treatment indicates that the medical team must determine whether EEG-brain wave activity is present at step 368. The patient has pre-selected whether he or she desires treatment to be removed if there has been no recovery and there is no EEG-brain wave activity or whether additional treatment is desired. In the case of removal of treatment at step 352, death occurs and organ donation is evaluated at steps 350, 351. If additional treatment is required, then the medical team proceeds to continue long-term critical care treatment at step 369.

The present invention extends to computer programs in the form of source code, object code, code intermediate sources and partially compiled object code, or in any other form suitable for use in the implementation of the invention. Computer programs are suitably standalone applications, software components, scripts or plug-ins to other applications. Computer programs embedding the invention are advantageously embodied on a carrier, being any entity or device capable of carrying the computer program: for example, a storage medium such as ROM or RAM, optical recording media such as CD-recording media such as CD-ROM, magnetic recording media such as floppy discs or USB's, DVD's which are easily transportable with the individual. The carrier is any transmissible carrier such as an electrical or optical signal conveyed by electrical or optical cable, or by radio or any other manner. Computer programs are suitably downloaded across the Internet from a server. Computer programs are also capable of being embedded in an integrated circuit. Any and all such embodiments containing code that will cause a computer to substantially perform the invention principles of the present invention as described will fall within the scope of the invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. An interactive computer-implemented method for generating storing and retrieving a customized document for authorizing medical care instructions pertaining to the level of care to be provided at a future time to an individual by medical professionals, the level of care being selected, created and customized by the individual based upon the specific medical requirements and desires of the individual stored in the memory of a computer system when executed by a processor of the computer system, said method comprising the steps of:

provuing from the memory of the computer system health and medical information and health and medical education in non-professional terminology to the individual, said health and medical education and information comprising respective medical care for a particular set of medical circumstances, legal terms and medical procedures;

selecting from the memory of the computer system requirements for addressing pre-selected medical emergencies and medical situations, said health and medical information and education informing and educating the individual in non-medical and/or non-legal terminology for facilitating the ability of the individual to understand the health and medical information and education and for facilitating the ability of the individual to select the proper level of medical care that is desired by the individual depending on a particular one of selected medical emergencies or medical situations, and the health and medical education and information educating the individual regarding various potential outcomes of a particular medical care decision;

inputting and electronically capturing and processing personal information into the computer system, the personal information comprising specific particular medical care desired of the individual depending on the particular medical emergency or situation circumstances stored in the memory of the computer, and inputting personal information into the computer system based on the health and medical education and information;

providing customized individualized data in response to a request therefor for obtaining particular relevant required personal information of the individual based on medical and personal information processed by and stored in the memory of the computer system;

recording decisions of the individual by the processor of the computer system, the decisions comprising particular electronic instructions for the specific particular medical care for rendering medical care decisions on a selected level of medical care in accordance with said particular electronic instructions based on the personal information of the individual stored in the memory of the computer system;

placing, by the processor of the computer system, the particular medical care decisions of the individual into compliance with relevant state and Federal laws electronically stored in the memory of the computer system, and processing relevant state or Federal laws relative to the medical care decisions of the individual and electronically harmonizing the medical care decisions of the individual with the relevant state or federal laws stored in the memory of the computer system to ensure the medical care decisions comply with the relevant state or Federal laws;

electronically integrating by the processor of the computer system all related data and information inputted into the computer system for creating medical care instructions for the individual for the particular medical emergency or situation in electronic format;

creating medical care instructions by the processor of the computer system in response to the inputted data and information of the individual from the step of processing the inputted data and information of the personal information of the individual to create medical instructions and transmitting the inputted data and information into the computer system;

providing the processed generated medical care instructions to the individual to enable the individual to immediately review the created medical care instructions and to revise the created medical care instructions according to the changing age, condition, morals and beliefs of the individual;

storing, retrieving and processing the generated medical care instructions by the processor of the computer system for readily available accessibility of the medical care instructions by medical personnel in real-time; and updating, maintaining and processing the medical care instructions by the processor of the computer system periodically to generate a reminder signal for reminding the individual to update and maintain the level of medical care decisions according to a pre-set schedule, and for automatically updating the level of medical care decisions according to any changes in the relevant state and Federal laws.

2. The method according to claim 1, further comprising the step of electronically outputting said medical care instructions and with updated state and Federal laws from the memory of the computer system.

3. The method according to claim 1, wherein said the step of inputting and electronically capturing the personal information is selected from the group consisting of obtaining information about said individual and inputting the information about said individual into a computer, providing questions by the computer system to be answered by the individual, providing questions by the computer system and providing the questions on a website to be answered by the individual, and providing questions by the computer system in paper-form to be answered by the individual and being electronically scannable into a computer.

4. The method according to claim 3, wherein said questions provided on a computer program are provided to the individual in a form selected from the group consisting of a CD-ROM and an Internet website.

5. The method according to claim 1, wherein the step of providing medical and health information and education to the individual by the computer system comprises providing video for discussion of emergency medical care and scenarios, discussion of possible outcomes, risks and benefits of particular medical care decisions and procedures and medical conditions, demonstrating medical care techniques and procedures, explaining legal terminology, and explaining medical procedures and medical terminology.

6. The method according to claim 5, wherein the step of providing medical and health information and education to the individual by the computer system is selected from the group consisting of providing information by a CD-ROM and providing information by an Internet website.

7. The method according to claim 1, wherein said step of recording decisions of the individual by the computer system comprises preparing medical care decisions for the individual based on information obtained by the individual.

8. The method according to claim 7, wherein said step of recording decisions by the individual by the computer system further comprises providing expert medical rules and expert legal rules to which medical care decisions are applied.

9. The method according to claim 1, wherein said step of creating medical care instructions by the computer system comprises creating the medical care instructions in at least one form selected from the group consisting of paper form and electronic form.

10. The method according to claim 9, wherein the individual provides an electronic signature when the medical care instructions are provided in electronic form.

11. The method according to claim 2, wherein said step of outputting the medical care instructions by the computer system comprises outputting in at least one form selected from the group consisting of paper form and electronic form.

12. The method according to claim 11, wherein the individual provides an electronic signature when the medical care instructions are provided in electronic form.

13. The method according to claim 1, wherein the step of storing, retrieving and processing the medical care instructions by the computer system comprises using a storage medium selected from the group consisting of optical storage, magnetic storage, a CD-ROM, a central database accessible by a website, a central repository, paper form, a computer chip, radio frequency identification (RFID), a pen-drive and a barcode tag.

14. The method according to claim 13, wherein the step of storing, retrieving and processing the medical care instructions by the computer system comprises immediate accessibility of the medical care instructions by the individual or by authorized medical personnel at any time via a secure computer network and in real-time.

15. The method according to claim 1, further comprising the step of scanning medical care instructions into the computer system by a scanning device when the medical care instructions are in paper form for electronic storage and processing in the computer system.

16. The method according to claim 1, wherein the personal information of the individual by the computer system is at least one selected from the group consisting of legal information, powers of attorney, insurance information, patient health information, medical care information, patient family and contact information, patient social security number and patient fingerprint information.

17. The method according to claim 1, wherein the step of reminding the individual for updating and maintaining the medical care instructions by the computer system periodically reminds the individual that updates and maintenance of the medical care instructions are necessary by at least one mechanism selected from the group consisting of electronic mail, regular mail and telephonic contact.

* * * * *